(12) United States Patent
Kovach et al.

(10) Patent No.: US 10,413,541 B2
(45) Date of Patent: *Sep. 17, 2019

(54) OXABICYCLOHEPTANES AND OXABICYCLOHEPTENES FOR THE TREATMENT OF DEPRESSIVE AND STRESS DISORDERS

(71) Applicant: LIXTE BIOTECHNOLOGY, INC., East Setauket, NY (US)

(72) Inventors: John S. Kovach, East Setauket, NY (US); Salvatore Lecca, Paris (FR); Manuel Mameli, Paris (FR)

(73) Assignee: Lixte Biotechnology, Inc., Setauket, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,372

(22) Filed: Nov. 17, 2017

(65) Prior Publication Data

US 2018/0256565 A1    Sep. 13, 2018

Related U.S. Application Data

(63) Continuation of application No. 15/048,389, filed on Feb. 19, 2016, now Pat. No. 9,833,450.

(60) Provisional application No. 62/279,265, filed on Jan. 15, 2016, provisional application No. 62/118,246, filed on Feb. 19, 2015.

(51) Int. Cl.
| | |
|---|---|
| *A61K 31/496* | (2006.01) |
| *A61K 31/343* | (2006.01) |
| *C07D 493/08* | (2006.01) |
| *C07D 303/32* | (2006.01) |

(52) U.S. Cl.
CPC .......... *A61K 31/496* (2013.01); *A61K 31/343* (2013.01); *C07D 303/32* (2013.01); *C07D 493/08* (2013.01)

(58) Field of Classification Search
None
See application file for complete search history.

(56) References Cited

U.S. PATENT DOCUMENTS

| | | | |
|---|---|---|---|
| 4,361,436 A | 11/1982 | McCarthy et al. | |
| 4,614,825 A | 9/1986 | Snitman et al. | |
| 4,713,453 A | 12/1987 | Tatsuoka et al. | |
| 4,900,723 A | 2/1990 | Schumacher | |
| 4,931,460 A | 6/1990 | Grover et al. | |
| 6,440,726 B1 | 8/2002 | Resnick | |
| 7,998,957 B2 | 8/2011 | Kovach et al. | |
| 8,058,268 B2 | 11/2011 | Kovach | |
| 8,143,445 B2 | 3/2012 | Kovach et al. | |
| 8,227,473 B2 | 7/2012 | Kovach et al. | |
| 8,329,719 B2 | 12/2012 | Kovach | |
| 8,426,444 B2 | 4/2013 | Kovach et al. | |
| 8,455,688 B2 | 6/2013 | Kovach et al. | |
| 8,541,458 B2 | 9/2013 | Kovach et al. | |
| 8,822,461 B2 | 9/2014 | Kovach et al. | |
| 9,079,917 B2 | 7/2015 | Kovach et al. | |
| 9,526,915 B2* | 12/2016 | Kovach | A61K 31/44 |
| 2003/0171255 A1 | 9/2003 | Greengard et al. | |
| 2005/0049352 A1 | 3/2005 | Rubinsztajn et al. | |
| 2005/0131106 A1 | 6/2005 | Tonapi et al. | |
| 2005/0170188 A1 | 8/2005 | Campbell et al. | |
| 2005/0266263 A1 | 12/2005 | Campbell et al. | |
| 2006/0147719 A1 | 7/2006 | Rubinsztajn et al. | |
| 2008/0249130 A1 | 10/2008 | Vu | |
| 2009/0035292 A1 | 2/2009 | Kovach et al. | |
| 2009/0143445 A1 | 6/2009 | Kovach et al. | |
| 2010/0029484 A1 | 2/2010 | Kovach et al. | |
| 2010/0029640 A1 | 2/2010 | Kovach | |
| 2011/0273646 A1 | 11/2011 | Fukagawa et al. | |
| 2012/0129826 A1 | 5/2012 | Henn | |
| 2012/0135522 A1 | 5/2012 | Kovach | |
| 2013/0197044 A1 | 8/2013 | Pavliv et al. | |
| 2013/0280210 A1 | 10/2013 | Kovach | |
| 2014/0193632 A1 | 7/2014 | Saito et al. | |
| 2014/0274712 A1 | 9/2014 | Finnessy et al. | |
| 2015/0148353 A1 | 5/2015 | Kovach | |

(Continued)

FOREIGN PATENT DOCUMENTS

| | | |
|---|---|---|
| WO | WO 2007092414 A2 | 8/2007 |
| WO | WO 2008097561 A1 | 8/2008 |

(Continued)

OTHER PUBLICATIONS

International Search Report issued in connection with PCT International Application No. PCT/US2016/018679, dated May 17, 2016, 4 pages.

(Continued)

*Primary Examiner* — Kamal A Saeed
(74) *Attorney, Agent, or Firm* — Andrea L. C. Reid; Dechert LLP

(57) ABSTRACT

A method of treating a depressive or stress disorder in a subject afflicted therewith comprising administering to the subject an effective amount of a compound having the structure:

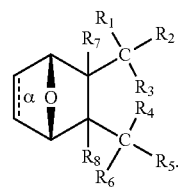

20 Claims, 16 Drawing Sheets

(56) References Cited

U.S. PATENT DOCUMENTS

| | | | |
|---|---|---|---|
| 2015/0174123 | A1 | 6/2015 | Kovach |
| 2015/0328190 | A1 | 11/2015 | Pavliv et al. |
| 2016/0051544 | A1 | 2/2016 | Kovach et al. |
| 2016/0074390 | A1 | 3/2016 | Kovach |
| 2016/0333024 | A1 | 11/2016 | Kovach |

FOREIGN PATENT DOCUMENTS

| | | | |
|---|---|---|---|
| WO | WO 2009020565 A1 | 2/2009 | |
| WO | WO 2009045440 A1 | 4/2009 | |
| WO | WO 2010014141 A1 | 2/2010 | |
| WO | WO 2010014220 A1 | 2/2010 | |
| WO | WO 2010014254 A1 | 2/2010 | |
| WO | WO 2010147612 A1 | 12/2010 | |
| WO | WO 2012162535 A1 | 11/2012 | |
| WO | WO 2014005080 A1 | 1/2014 | |
| WO | WO 2014005084 A1 | 1/2014 | |
| WO | WO 2014137741 A1 | 9/2014 | |
| WO | WO 2014149494 A1 | 9/2014 | |
| WO | WO 2014168941 A1 | 10/2014 | |
| WO | WO 2015073802 A1 | 5/2015 | |
| WO | WO 2015196073 A1 | 12/2015 | |
| WO | WO 2016014783 A1 | 1/2016 | |
| WO | WO 2016040877 A1 | 3/2016 | |
| WO | WO 2016061193 A1 | 4/2016 | |
| WO | WO 2016134257 A1 | 8/2016 | |
| WO | WO 2016186963 A1 | 11/2016 | |

OTHER PUBLICATIONS

Written Opinion of the International Searching Authority issued in connection with PCT International Application No. PCT/US2016/018679, dated May 17, 2016, 6 pages.

Alcami et al., "Measuring the firing rate of high-resistance neurons with cell-attached recording," J Neurosci, 32(9):3118-30 (Feb. 2012).

Anisman et al., "Multiple neurochemical and behavioral consequences of stressors: implications for depression," Pharmacol Ther, 46(1):119-36 (1990).

Arora et al., "Acute cocaine exposure weakens GABAB receptor-dependent Girk signaling in dopamine neurons of the ventral tegmental area," J Neurosci, 31(34):12251-12257 (Aug. 2011).

Bagdy et al., "A new clinical evidence-based gene-environment interaction model of depression," Neuropsychopharmacol Hung, 14(4):213-20 (Dec. 2012).

Balana et al., "Mechanism underlying selective regulation of G protein-gated inwardly rectifying potassium channels by the psychostimulant-sensitive sorting nexin 27," Proc Natl Acad Sci USA, 108(14):5831-6 (Apr. 2011).

Belin et al., "Cocaine seeking habits depend upon dopamine-dependent serial connectivity linking the ventral with the dorsal striatum," Neuron, 57(3):432-41 (Feb. 2008).

Berge et al., "Pharmaceutical Salts," J Pharm Sci, 66:1-19 (1977).

Bleich et al., "Post-traumatic stress disorder and depression. An analysis of comorbidity," Br J Psychiatry, 170:479-82 (May 1997).

Boyer et al., "Direct interaction of GABAB receptors with M2 muscarinic receptors enhances muscarinic signaling," J Neurosci, 29(50):15796-809 (Dec. 2009).

Buynitsky et al., "Restraint stress in biobehavioral research: Recent developments," Neurosci Biobehav Rev, 33(7):1089-98 (Jul. 2009).

Chen et al., "Cocaine but not natural reward self-administration nor passive cocaine infusion produces persistent LTP in the VTA," Neuron, 59(2):288-97 (Jul. 2008).

Clancy et al., "Coregulation of natively expressed pertussis toxin-sensitive muscarinic receptors with G-protein-activated potassium channels," J Neurosci, 27(24):6388-99 (Jun. 2007).

Cornelisse et al., "Reduced 5-HT1A-and GABAB receptor function in dorsal raphé neurons upon chronic fluoxetine treatment of socially stressed rats," J Neurophysiol, 98(1):196-204 (Jul. 2007).

Gonzalez-Maeso, "Agonist-induced desensitization and endocytosis of heterodimeric GABAB receptors in CHO-K1 cells," Eur J Pharmacol, 481(1):15-23 (Nov. 2003).

Guetg et al., "NMDA receptor-dependent GABAB receptor internalization via CaMKII phosphorylation of serine 867 in GABAB1," Proc Natl Acad Sci USA, 107(31):13924-9 (Aug. 2010).

Hammack et al., "Overlapping neurobiology of learned helplessness and conditioned defeat: implications for PTSD and mood disorders," Neuropharmacology, 62(2):565-75 (Feb. 2012).

Hearing et al., "Repeated cocaine weakens GABA(B)-Girk signaling in layer 5/6 pyramidal neurons in the prelimbic cortex," Neuron, 80(1):159-70 (Oct. 2013).

Hibino et al., "Anchoring proteins confer G protein sensitivity to an inward-rectifier K(+) channel through the GK domain," EMBO J, 19(1):78-83 (Jan. 2000).

Hikosaka, "The habenula: from stress evasion to value-based decision-making.," Nat Rev Neurosci, 11(7):503-13 (Jul. 2010).

Jhou et al., "The rostromedial tegmental nucleus (RMTg), a GABAergic afferent to midbrain dopamine neurons, encodes aversive stimuli and inhibits motor responses," Neuron, 61(5):786-800 (Mar. 2009).

Jhou et al., "Cocaine Drives Aversive Conditioning via Delayed Activation of Dopamine-Responsive Habenular and Midbrain Pathways," J Neurosci, 33(17):7501-7512 (Apr. 2013).

Knoll et al., "Dynorphin, stress, and depression," Brain Res, 1314:56-73 (Feb. 2010).

Labouebe et al., "RGS2 modulates coupling between GABAB receptors and GIRK channels in dopamine neurons of the ventral tegmental area," Nat Neurosci, 10(12):1559-68 (Dec. 2007).

Lalive et al., "Firing modes of dopamine neurons drive bidirectional GIRK channel plasticity," J Neurosci, 34(15):5107-14 (Apr. 2014).

Lammel et al., "Input-specific control of reward and aversion in the ventral tegmental area," Nature, 491(7423):212-7 (Nov. 2012).

Lauffer et al., "SNX27 mediates PDZ-directed sorting from endosomes to the plasma membrane," J Cell Biol, 190(4):565-74 (Aug. 2010).

Lavine et al., "G protein-coupled receptors form stable complexes with inwardly rectifying potassium channels and adenylyl cyclase," J Biol Chem, 277(48):46010-9 (Nov. 2002).

Lecca et al., "The lateral habenula in addiction and depression: an anatomical, synaptic and behavioral overview," Eur J Neurosci, 39(7):1170-8 (Apr. 2014).

Lemos et al., "Repeated stress dysregulates κ-opioid receptor signaling in the dorsal raphe through a p38α MAPK-dependent mechanism," J Neurosci, 32(36):12325-36 (Sep. 2012).

Lemos et al., "Severe stress switches CRF action in the nucleus accumbens from appetitive to aversive," Nature, 490(7420):402-6 (Oct. 2012).

Leonoudakis et al., "A multiprotein trafficking complex composed of SAP97, CASK, Veli, and Mint1 is associated with inward rectifier Kir2 potassium channels," J Biol Chem 279(18):19051-63 (Apr. 2004).

Leyland et al., "An alternatively spliced isoform of PSD-93/chapsyn 110 binds to the inwardly rectifying potassium channel, Kir2.1," J Biol Chem, 279(42):43427-36 (Oct. 2004).

Li et al., "Synaptic potentiation onto habenula neurons in the learned helplessness model of depression," Nature, 470(7335):535-9 (Feb. 2011).

Li et al., "βCaMKII in lateral habenula mediates core symptoms of depression," Science, 341(6149):1016-20 (Aug. 2013).

Logothetis et al., "The beta gamma subunits of GTP-binding proteins activate the muscarinic K+ channel in heart," Nature, 325(6102):321-6 (Jan. 1987).

Lu et al., "The effect of a PP2A inhibitor on the nuclear receptor corepressor pathway in glioma.," J Neurosurg, 113(2):225-33 (Aug. 2010).

Lu et al., "Inhibition of serine/threonine phosphatase PP2A enhances cancer chemotherapy by blocking DNA damage induced defense mechanisms," Proc Natl Acad Sci USA, 106(28):11697-702 (Jul. 2009).

Lujan et al., "New insights into the therapeutic potential of Girk channels," Trends Neurosci, 37(1):20-9 (Jan. 2014).

Lunn et al., "A unique sorting nexin regulates trafficking of potassium channels via a PDZ domain interaction," Nat Neurosci, 10(10):1249-59 (Oct. 2007).

(56) References Cited

OTHER PUBLICATIONS

Luscher et al., "G protein-coupled inwardly rectifying K+ channels (GIRKs) mediate postsynaptic but not presynaptic transmitter actions in hippocampal neurons," Neuron, 19(3):687-95 (Sep. 1997).

Luscher et al., "Emerging roles for G protein-gated inwardly rectifying potassium (GIRK) channels in health and disease," Nat Rev Neurosci, 11(5):301-15 (May 2010).

Luthi et al., "Pathological circuit function underlying addiction and anxiety disorders," Nat Neurosci, 17(12):1635-43 (Dec. 2014).

Mameli et al., "Cocaine-evoked synaptic plasticity: persistence in the VTA triggers adaptations in the Nac," Nat Neurosci, 12(8):1036-41 (Aug. 2009).

Mao et al., "Molecular basis for the inhibition of G protein-coupled inward rectifier K(+) channels by protein kinase C," Proc Natl Acad Sci USA, 101(4):1087-92 (Jan. 2004).

Martiniova et al., "Pharmacologic modulation of serine/threonine phosphorylation highly sensitizes PHEO in a MPC cell and mouse model to conventional chemotherapy," PLoS One, 6(2):e14678 (Feb. 2011).

Matsumoto et al., "Lateral habenula as a source of negative reward signals in dopamine neurons," Nature, 447(7148):1111-5 (Jun. 2007).

Mauna et al., "Protein phosphatases 1 and 2 are both required for long-term depression and associated dephosphorilation of cAMP response element binding protein in hippocampal área CA1 in vivo", Hippocampus 2010, vol. 21, No. 10, 1093-1104.

Meye et al., "Cocaine-evoked negative symptoms require AMPA receptor trafficking in the lateral habenula," Nat Neurosci, 18(3):376-8 (Mar. 2015).

Nehring et al., "Neuronal inwardly rectifying K(+) channels differentially couple to PDZ proteins of the PSD-95/SAP90 family," J Neurosci, 20(1):156-62 (Jan. 2000).

Nobles et al., "Heterotrimeric G proteins precouple with G protein-coupled receptors in living cells," Proc Natl Acad Sci USA, 102(51):18706-11 (Dec. 2005).

Padgett et al., "Methamphetamine-evoked depression of GABA(B) receptor signaling in GABA neurons of the VTA," Neuron, 73(5):978-89 (Mar. 2012).

Pinard et al., "GABAB receptors: physiological functions and mechanisms of diversity," Adv Pharmacol, 58:231-55 (2010).

Porsolt et al., "Behavioral despair in mice: a primary screening test for antidepressants," Arch Int Pharmacodyn Ther, 229(2):327-36 (Oct. 1977).

Proulx et al., "Reward processing by the lateral habenula in normal and depressive behaviors," Nat Neurosci, 17(9):1146-52 (Sep. 2014).

Rittenhouse et al., "Amplified behavioral and endocrine responses to forced swim stress in the Wistar-Kyoto rat," Psychoneuroendocrinology, 27(3):303-18 (Apr. 2002).

Riven et al., "GIRK channel activation involves a local rearrangement of a preformed G protein channel complex," Neuron, 51(5):561-73 (Sep. 2006).

Shabel et al., "Mood regulation. GABA/glutamate co-release controls habenula output and is modified by antidepressant treatment," Science, 345(6203):1494-8 (Sep. 2014).

Stamatakis et al., "Activation of lateral habenula inputs to the ventral midbrain promotes behavioral avoidance," Nat Neurosci, 15(8):1105-7 (Jun. 2012).

Sugaya et al., "Role of GIRK Channels in Addictive Substance Effects", Journal of Drug and Alcohol Research 2013, vol. 2, 1-11.

Takahashi et al., "The smell of danger: a behavioral and neural analysis of predator odor-induced fear," Neurosci Biobehav Rev, 29(8):1157-67 (2005).

Terunuma et al., "Functional modulation of GABAB receptors by protein kinases and receptor trafficking," Adv Pharmacol, 58:113-22 (2010).

Tiao et al., "The sushi domains of secreted GABA(B1) isoforms selectively impair GABA(B) heteroreceptor function,"J Biol Chem. Nov. 7, 2008;283(45):31005-11, J Biol Chem, 283(45):31005-11 (Nov. 2008).

Tye et al., "Dopamine neurons modulate neural encoding and expression of depression-related behaviour," Nature, 493(7433):537-541 (Jan. 2013).

Zhang, et al., "A synthetic cantharidin analog for the enhancement of doxorubicin suppression of stem cell-derived aggressive sarcoma," Biomaterials, 31(36):9535-43 (Dec. 2010).

Zucker et al., "Short-term synaptic plasticity," Annu Rev Physiol, 64:355-405 (2002).

\* cited by examiner

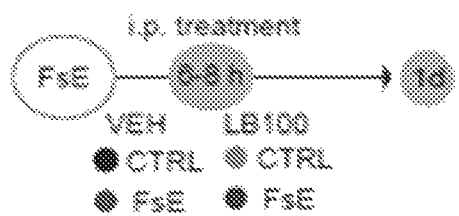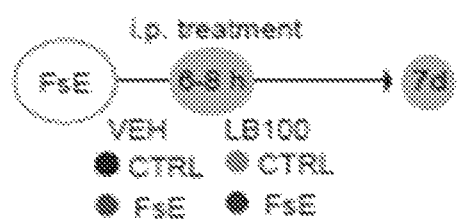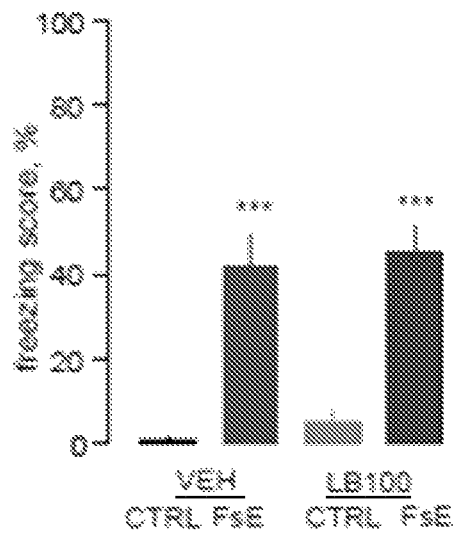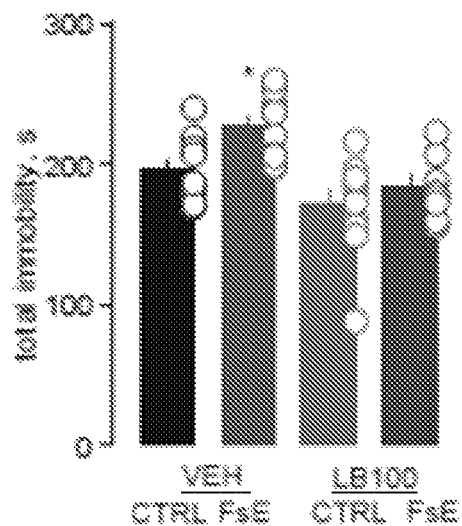
Fig. 7F-7G

OXABICYCLOHEPTANES AND OXABICYCLOHEPTENES FOR THE TREATMENT OF DEPRESSIVE AND STRESS DISORDERS

This application is a continuation of U.S. patent application Ser. No 15/048,389, filed Feb. 19, 2016, now U.S. Pat. No. 9,833,450, which claims the benefit of U.S. Provisional Patent Application Nos. 62/279,265, filed Jan. 15, 2016; and 62/118,246, filed Feb. 19, 2015, the contents of each of which are hereby incorporated by reference.

Throughout this application various publications are referenced. The disclosures of these documents in their entireties are hereby incorporated by reference into this application in order to more fully describe the state of the art to which this invention pertains.

BACKGROUND OF THE INVENTION

Unpredicted aversive stimuli trigger rapid emotional and behavioral reactions, and if persistent, may contribute to the emergence of depressive-like symptoms in both animals and humans (Knoll and Carlezon, 2010). The lateral habenula (LHb) processes aversive stimuli and disappointment and drives aversive behaviors (Matsumoto and Hikosaka, 2007; Stamatakis and Stuber, 2012). The LHb has been implicated in addiction (Lecca, S. et al. 2014).

Aversive stimuli, and more generally stressors, increase the activity of LHb neurons projecting to monoaminergic centers including the ventral tegmental area and the raphe nucleus (Hikosaka, 2010; Matsumoto and Hikosaka, 2007; Proulx et al., 2014). Indeed in mice exposed to foot-shocks, the EPSC paired pulse ratio obtained by optogenetic driven activation of LHb terminals onto midbrain GABA neurons is rapidly decreased indicating a higher glutamate release from LHb axons to midbrain neuronal populations (Stamatakis and Stuber, 2012). The repetitive exposure to aversive environmental stimuli produces instead an aberrant and persistent hyperactivity of LHb neurons, which has been proven instrumental for the emerging of depressive symptoms (Li et al., 2011; Li et al., 2013) (Meye, Valentinova, Lecca et al., 2015).

The underlying mechanisms implicate distinct mechanisms; firstly a CaMKIIβ- and GluA1-dependent strengthening of AMPA-mediated transmission (Li et al., 2013) (Meye, Valentinova, Lecca et al., 2015); and secondly a reduction in the GABA component of GABA-Glutamate co-release typical of the entopeduncular nucleus-to-LHb synapse (Proulx et al., 2014; Shabel et al., 2014). Altogether, these findings indicate that the induction and maintenance of depressive behaviors may require complex and temporally distinct synaptic modifications relying on specific inputs and outputs of LHb neurons (Lecca et al., 2014).

Neuronal excitability throughout the central nervous system relies, at least in part, on the slow GABA-dependent inhibition mediated by GABAB receptors (GABABRs) and G protein-gated inwardly rectifying potassium (GIRK/Kir3) channels (Luscher et al., 1997). Repeated stressful events lead to the dysregulation of GIRK-dependent signaling (Lemos et al., 2012a; Lemos at al., 2012b). Furthermore, analysis of GIRK gene expression and function in rodents (Cornelisse et al., 2007; Lujan et al., 2014), and polymorphisms in the GIRK gene in human cohorts provide strong arguments for GABAB-GIRK implications in the development of depressive symptoms (Bagdy et al., 2012).

SUMMARY OF THE INVENTION

The present invention provides a method of treating a depressive or stress disorder in a subject afflicted therewith comprising administering to the subject an effective amount of a compound having the structure:

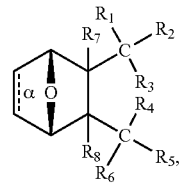

wherein
bond α is present or absent;
$R_1$ and $R_2$ together are =O;
$R_3$ is OH, O$^-$, OR$_9$, O(CH$_2$)$_{1-6}$R$_9$, SH, S$^-$, or SR$_9$, wherein R$_9$ is H, alkyl, alkenyl, alkynyl or aryl;
$R_4$ is

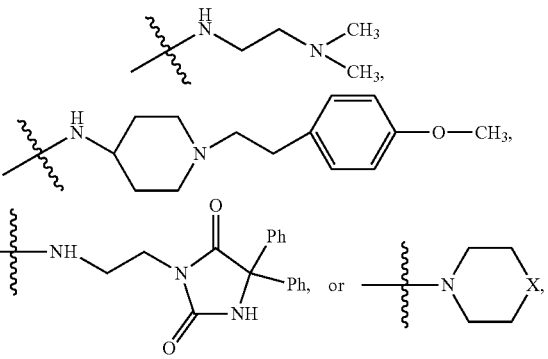

where X is O, S, NR$_{10}$, N$^+$HR$_{10}$ or N$^+$R$_{10}$R$_{10}$,
where each R$_{10}$ is independently H, alkyl, alkenyl, alkynyl, aryl,

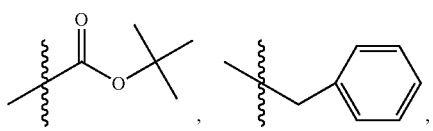

—CH$_2$CN, —CH$_2$CO$_2$R$_{11}$, or —CH$_2$COR$_{11}$,
wherein each R$_{11}$ is independently H, alkyl, alkenyl or alkynyl;
$R_5$ and $R_6$ taken together are =O;
$R_7$ and $R_8$ are each H,
or a salt, zwitterion, or ester thereof, so as to thereby treat the depressive or stress disorder in the subject.

The present invention also provides a method of preventing or reducing the severity of a depressive or stress disorder in a subject following a traumatic event comprising:

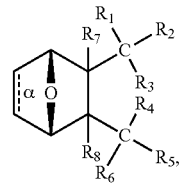

wherein
bond α is present or absent;
$R_1$ and $R_2$ together are =O;
$R_3$ is OH, O⁻, $OR_9$, $O(CH_2)_{1-6}R_9$, SH, S⁻, or $SR_9$,
  wherein $R_9$ is H, alkyl, alkenyl, alkynyl or aryl;
$R_4$ is

[chemical structure]

[chemical structure]

[chemical structure]

where X is O, S, $NR_{10}$, $N^+HR_{10}$ or $N^+R_{10}R_{10}$,
  where each $R_{10}$ is independently H, alkyl, alkenyl, alkynyl,
  aryl,

[chemical structure], [chemical structure],

—$CH_2CN$, —$CH_2CO_2R_{11}$, or —$CH_2COR_{11}$,
  wherein each $R_{11}$ is independently H, alkyl, alkenyl or alkynyl;
$R_5$ and $R_6$ taken together are =O;
$R_7$ and $R_8$ are each H,
or a salt, zwitterion, or ester thereof, so as to thereby prevent or reduce the severity of the depressive or stress disorder in a subject following a traumatic event.

The present invention further provides a method of treating addiction in a subject afflicted therewith comprising administering to the subject an effective amount of a compound having the structure:

[chemical structure]

wherein
bond α is present or absent;
$R_1$ and $R_2$ together are =O;
$R_3$ is OH, O⁻, $OR_9$, $O(CH_2)_{1-6}R_9$, SH, S⁻, or $SR_9$,
  wherein $R_9$ is H, alkyl, alkenyl, alkynyl or aryl;
$R_4$ is

[chemical structure]

[chemical structure]

[chemical structure]

where X is O, S, $NR_{10}$, $N^+HR_{10}$ or $N^+R_{10}R_{10}$,
  where each $R_{10}$ is independently H, alkyl, alkenyl, alkynyl,
  aryl,

[chemical structure], [chemical structure],

—$CH_2CN$, —$CH_2CO_2R_{11}$, or —$CH_2COR_{11}$,
  wherein each $R_{11}$ is independently H, alkyl, alkenyl or alkynyl;
$R_5$ and $R_6$ taken together are =O;
$R_7$ and $R_8$ are each H,
or a salt, zwitterion, or ester thereof, so as to thereby treat the addiction in the subject.

BRIEF DESCRIPTION OF THE FIGURES

FIG. 7F: In vivo inhibition of PP2A activity rescues GABAB-GIRK function, the hyperexcitability and FsE-driven depressive-like phenotype. LB100 ip treatment did not affect the freezing score in the re-exposure to the context test.

FIG. 7G: In vivo inhibition of PP2A activity rescues GABAB-GIRK function, the hyperexcitability and FsE-driven depressive-like phenotype. Bar graph showing that LB100 ip treatment 6-8 h after the FsE is sufficient to rescue the impairment in the Forced swim test.

DETAILED DESCRIPTION OF THE INVENTION

Figures 1A, 1B, 1C:
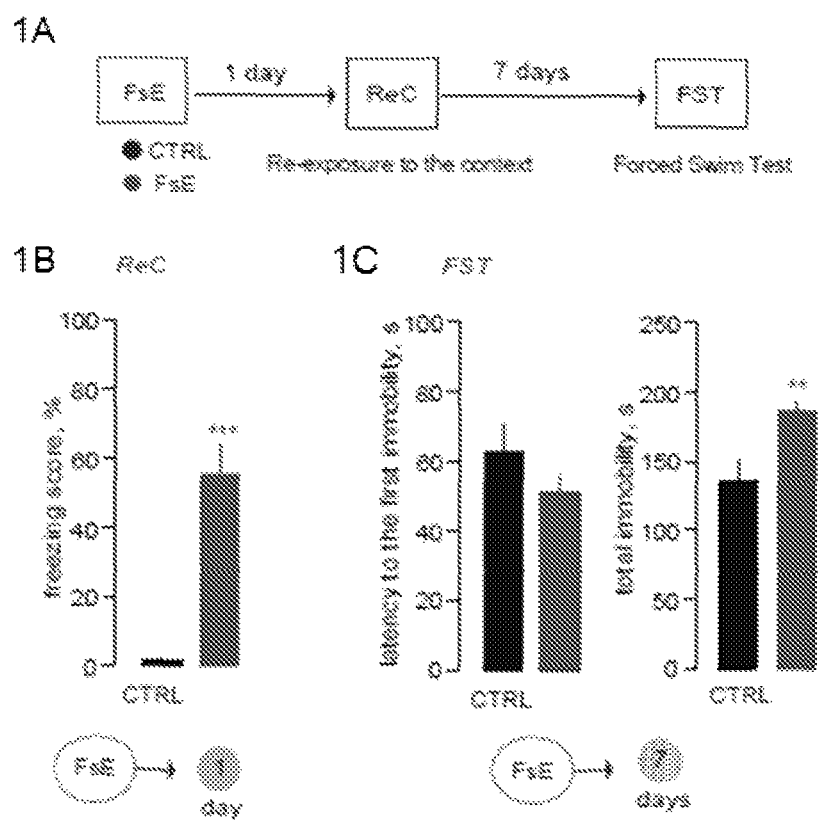
FIG. 1A: FsE-induced depressive-like phenotype and neuronal hyperexcitability in the LHb. Schematic summarizing the timeline of the behavioral tests. Footshock exposure (FsE) was followed by the re-exposure to the context (ReC) 1 day after and to the forced swim test (FST) 7 days later.
FIG. 1B: FsE-induced depressive-like phenotype and neuronal hyperexcitability in the LHb. Bar graph and scatter plots report the increase in the percentage of freezing in the FsE group compare to their control during the 5 m re-exposure to the operant chamber (CTRL vs FsE; n=8 vs 8; 1.25±0.82% vs 55.63±8.31%, t-test: t14-6.5; ***p<0.001)
FIG. 1C: FsE-induced depressive-like phenotype and neuronal hyperexcitability in the LHb. The FsE mice resulted impaired performing the FST 7 days after the procedure. The bar graph and scatter plots respectively report the reduction in the latency at the first episode of immobilization (left,) as well as the increased in the total time spent immobile (right, CTRL vs FsE; t-test, **p<0.01)

The present invention provides a method of treating a depressive or stress disorder in a subject afflicted therewith comprising administering to the subject an effective amount of a compound having the structure:

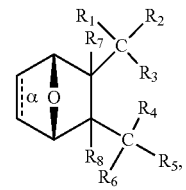

wherein bond α is present or absent;

$R_1$ and $R_2$ together are =O;

$R_3$ is OH, O$^-$, OR$_9$, O(CH$_2$)$_{1-6}$R$_9$, SH, S$^-$, or SR$_9$,
    wherein R$_9$ is H, alkyl, alkenyl, alkynyl or aryl;

$R_4$ is

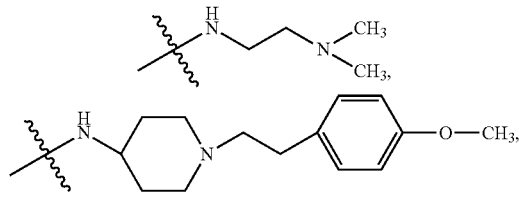

-continued

[chemical structure: hydantoin-ethyl-NH linker with two Ph groups], or [morpholine-type N-X structure]

where X is O, S, $NR_{10}$, $N^+HR_{10}$ or $N^+R_{10}R_{10}$,
where each $R_{10}$ is independently H alkyl, alkenyl, alkynyl,
aryl,

[ester linker structure], [benzyl structure],

—$CH_2CN$, —$CH_2CO_2R_1$, or —$CH_2COR_{11}$,
wherein each $R_{11}$ is independently H, alkyl, alkenyl or alkynyl;

$R_5$ and $R_6$ taken together are =O;
$R_7$ and $R_8$ are each H,
or a salt, zwitterion, or ester thereof, so as to thereby treat the depressive or stress disorder in the subject.

In some embodiments, the method wherein the amount of the compound is effective to reduce a clinical symptom of the depressive or stress disorder in the subject.

In some embodiments, the method wherein the treating comprises reducing the activity of the lateral habenula of the subject.

In some embodiments, the method wherein the treating comprises reducing the activity of neurons in the lateral habenula of the subject.

In some embodiments, the method wherein the treating comprises reducing neuronal hyperexcitability in the lateral habenula of the subject.

In some embodiments, the method wherein the treating comprises restoring normal GABAB-GIRK function in the lateral habenula of the subject.

In some embodiments, the method wherein the treating comprises inhibiting phosphatase activity in the lateral habenula of the subject.

The present invention also provides a method of preventing or reducing the severity of a depressive or stress disorder in a subject following a traumatic event comprising:

[bicyclic structure with substituents $R_1$, $R_2$, $R_3$, $R_4$, $R_5$, $R_6$, $R_7$, $R_8$, bond α, and O]

wherein
bond α is present or absent;
$R_1$ and $R_2$ together are =O;
$R_3$ is OH, O⁻, $OR_9$, $O(CH_2)_{1-6}R_9$, SH, S⁻, or $SR_9$,
wherein $R_9$ is H, alkyl, alkenyl, alkynyl or aryl;

$R_4$ is

[N-ethyl-N,N-dimethylamine structure],

[piperidine-ethyl-phenyl-O-$CH_3$ structure],

[hydantoin-ethyl-NH linker with two Ph groups], or [morpholine N-X], where X is O, S, $NR_{10}$, $N^+HR_{10}$ or $N^+R_{10}R_{10}$,
where each $R_{10}$ is independently H, alkyl, alkenyl, alkynyl,
aryl,

[ester linker structure], [benzyl structure],

—$CH_2CN$, —$CH_2CO_2R_{11}$, or —$CH_2COR_{11}$,
wherein each $R_{11}$ is independently H, alkyl, alkenyl or alkynyl;
$R_5$ and $R_6$ taken together are =O;
$R_7$ and $R_8$ are each H,
or a salt, zwitterion, or ester thereof, so as to thereby prevent or reduce the severity of the depressive or stress disorder in a subject following a traumatic event.

In some embodiments, the method wherein the amount of the compound is effective to reduce a clinical symptom of the depressive or stress disorder in the subject.

In some embodiments, the method wherein the preventing or reducing comprises reducing the activity of the lateral habenula of the subject.

In some embodiments, the method wherein the preventing or reducing comprises reducing the activity of neurons in the lateral habenula of the subject.

In some embodiments, the method wherein the preventing or reducing comprises reducing neuronal hyperexcitability in the lateral habenula of the subject.

In some embodiments, the method wherein the preventing or reducing comprises restoring normal GABAB-GIRK function in the lateral habenula of the subject.

In some embodiments, the method wherein the preventing or reducing comprises inhibiting phosphatase activity in the lateral habenula of the subject.

In some embodiments, the method wherein the depressive or stress disorder is a depressive disorder.

In some embodiments, the method wherein the depressive or stress disorder is a stress disorder.

In some embodiments, the method wherein the depressive disorder is major depression, dysthymia, postpartum depression, seasonal affective disorder, atypical depression, psychotic depression, bipolar disorder, premenstrual dysphoric disorder, situational depression or adjustment disorder with depressed mood.

In some embodiments, the method wherein the stress disorder is post-traumatic stress disorder (PTSD), acute stress disorder, generalized anxiety disorder (GAD), obsessive-compulsive disorder (OCD), panic disorder, social phobia or social anxiety disorder.

In some embodiments, the depressive or stress disorder is caused by an addictive substance.

In some embodiments, the depressive or stress disorder is caused by alcohol or cocaine.

In some embodiments, the depressive or stress disorder is induced by withdrawal from an addictive substance.

In some embodiments, the depressive or stress disorder is induced by withdrawal from alcohol or cocaine.

In some embodiments, the depressive or stress disorder is induced by discontinuing use of an addictive substance.

In some embodiments, the depressive or stress disorder is induced by discontinuing use of alcohol or cocaine.

In some embodiments, the subject is addicted to an addictive substance.

In some embodiments, the subject is addicted to alcohol or cocaine.

In some embodiments, the subject is suffering from withdrawal from the use an addictive substance.

In some embodiments, the subject is suffering from withdrawal from the use of alcohol or cocaine.

In some embodiments, the addictive substance is alcohol or cocaine.

The present invention further provides a method of treating addiction in a subject afflicted therewith comprising administering to the subject an effective amount of a compound having the structure:

wherein
bond α is present or absent;
$R_1$ and $R_2$ together are =O;
$R_3$ is OH, O⁻, $OR_9$, $O(CH_2)_{1-6}R_9$, SH, S⁻, or $SR_9$,
   wherein $R_9$ is H, alkyl, alkenyl, alkynyl or aryl
$R_4$ is where X is O, S, $NR_{10}$, $N^+HR_{10}$ or $N^+R_{10}R_{10}$,
   where each $R_{10}$ is independently H alkyl, alkenyl, alkynyl,
   aryl, —$CH_2CN$, —$CH_2CO_2R_{11}$, or —$CH_2COR_{11}$,
   wherein each $R_{11}$ is independently H, alkyl, alkenyl or alkynyl;
$R_5$ and $R_6$ taken together are =O;
$R_7$ and $R_8$ are each H,
or a salt, zwitterion, or ester thereof, so as to thereby treat the addiction in the subject.

In some embodiments, the addiction is alcohol addiction, drug addiction, stimulant addiction, or nicotine addiction.

In some embodiments, the addiction is cocaine addiction.

In some embodiments, the method wherein the compound has the structure:

In some embodiments, wherein bond α in the compound is present.

In some embodiments, wherein bond α in the compound is absent.

In some embodiments, wherein
$R_3$ is OH, O⁻, or $OR_9$,
   wherein $R_9$ is alkyl, alkenyl, alkynyl or aryl;
$R_4$ is where X is O, S, $NR_{10}$, $N^+HR_{10}$ or $N^+R_{10}R_{10}$,
   where each $R_{10}$ is independently H, alkyl, alkenyl, alkynyl,
   aryl, In some embodiments, wherein
wherein
R₃ is OH, O⁻ or OR₉,
  where R₉ is H, methyl, ethyl or phenyl.
In some embodiments, wherein
wherein
R₃ is OH, O⁻ or OR₉,
  wherein R₉ is methyl.
In some embodiments, wherein
wherein
R₄ is

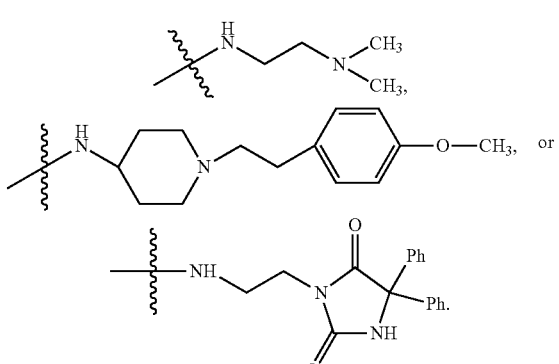

In some embodiments, wherein
wherein R₄ is

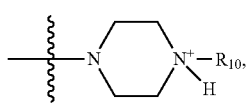

wherein R₁₀ is H, alkyl, alkenyl, alkynyl, aryl, or

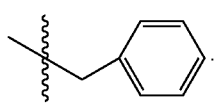

In some embodiments, wherein
wherein R₄ is

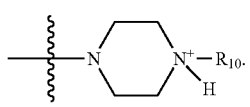

wherein R₁₀ is —H, —CH₃, —CH₂CH₃, or

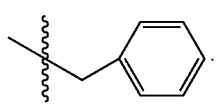 [SMILES: *Cc1ccccc1]

In some embodiments, wherein
wherein R₄ is

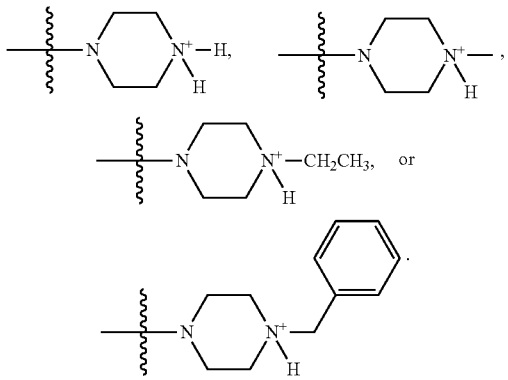

In some embodiments, wherein
wherein R₄ is

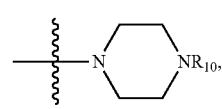

wherein R₁₀ is H, alkyl, alkenyl, alkynyl, aryl,

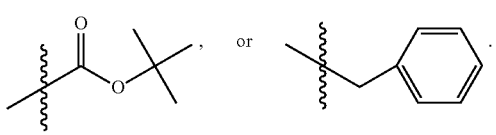

In some embodiments, wherein
wherein R₄ is

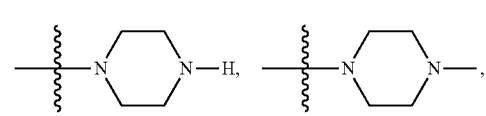

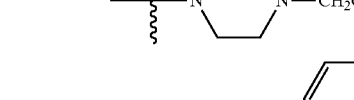

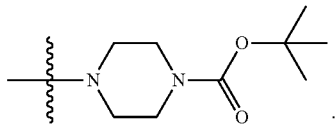

In some embodiments, wherein
wherein $R_4$ is

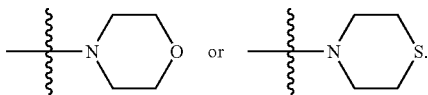 or ,

—$CH_2CN$, —$CH_2CO_2R_{12}$, or —$CH_2COR_{12}$,
where $R_{12}$ is H or alkyl,
or a salt, zwitterion or ester thereof.

In some embodiments, wherein the compound has the structure

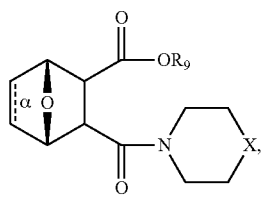

wherein
bond α is present or absent;
$R_9$ is present or absent and when present is H, alkyl, alkenyl, alkynyl or phenyl; and
X is O, $NR_{10}$, $NH^+R_{10}$ or $N^+R_{10}R_{10}$,
where each $R_{10}$ is independently H, alkyl, substituted alkyl, alkenyl, substituted alkenyl, alkynyl, substituted alkynyl, aryl,

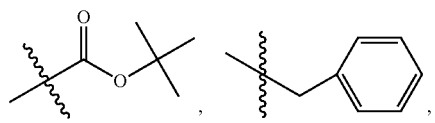,

—$CH_2CN$, —$CH_2CO_2R_{12}$, or —$CH_2COR_{12}$,
where $R_{12}$ is H or alkyl,
or a salt, zwitterion or ester thereof.

In some embodiments, wherein the compound has the structure

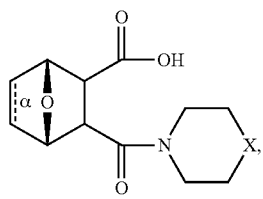

wherein
bond α is present or absent;
X is O or $NR_{10}$,
where each $R_{10}$ is independently H, alkyl, substituted alkyl, alkenyl, substituted alkenyl, alkynyl, substituted alkynyl, aryl,

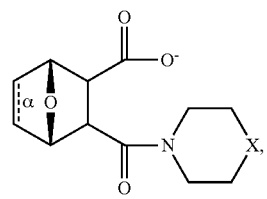

—$CH_2CN$, —$CH_2CO_2R_{12}$, or —$CH_2COR_{12}$,
where $R_{12}$ is H or alkyl,
or a salt, zwitterion or ester thereof.

In some embodiments, wherein the compound has the structure

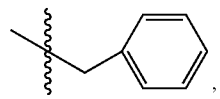

wherein
bond α is present or absent;
X is O or $NH^+R_{10}$,
where $R_{10}$ is H, alkyl, substituted alkyl, alkenyl, substituted alkenyl, alkynyl, substituted alkynyl, aryl,

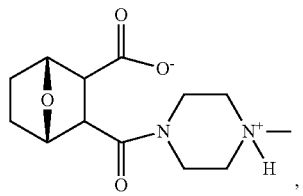 [SMILES: C[NH+]1CCN(C(=O)C2C(C(=O)[O-])[C@H]3CC[C@@H]2O3)CC1]

—$CH_2CN$, —$CH_2CO_2R_{12}$, or —$CH_2COR_{12}$.
where $R_{12}$ is H or alkyl,
or a salt, zwitterion or ester thereof.

In some embodiments, wherein the compound has the structure

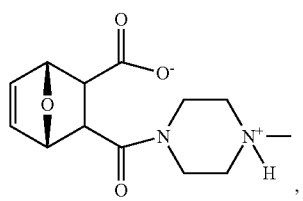

or a salt or ester thereof.

In some embodiments, wherein the compound has the structure

, or a salt or ester thereof.

In some embodiments, the method wherein the subject has been diagnosed with the depressive or stress disorder.

In some embodiments, the method wherein the subject has been affirmatively diagnosed with the depressive or stress disorder.

In some embodiments, the method wherein the subject has been affirmatively diagnosed with the depressive or stress disorder by psychological evaluation or by meeting the criteria in the Diagnostic and Statistical Manual of Mental Disorders.

In some embodiments, the method wherein the subject is a human.

In some embodiments, the method wherein the amount of the compound administered to the subject is 0.1 mg/m$^2$ to 5 mg/m$^2$.

In some embodiments, the method wherein the amount of the compound administered to the subject is 0.25 mg/m$^{z2}$ to 2.5 mg/m$^2$.

In some embodiments, the method wherein the amount of the compound administered to the subject is 2.5 mg/m$^2$ to 5 mg/m$^2$.

In some embodiments, the method wherein the amount of the compound administered to the subject is 3 mg/m$^2$ to 4.5 mg/m$^2$.

In some embodiments, the method wherein the amount of the compound administered to the subject is about 0.25 mg/m$^2$, 0.5 mg/m$^2$, 0.83 mg/m$^2$, 1.25 mg/m$^2$, 1.75 mg/m$^2$ or 2.33 mg/m$^2$.

In some embodiments, the method wherein the amount of the compound administered to the subject is about 0.25 mg/m$^2$, 0.5 mg/m$^2$, 0.75 mg/m$^2$, 1.0 mg/m$^2$, 1.25 mg/m$^2$, 1.5 mg/m$^2$, 1.75 mg/m$^2$, 2.0 mg/m$^2$, 2.25 mg/m$^2$, 2.5 mg/m$^2$ or 2.75 mg/m$^2$.

In some embodiments, the method wherein the amount of the compound administered to the subject is about 3 mg/m$^2$, 3.25 mg/m$^2$, 3.5 mg/m$^2$, 3.75 mg/m$^2$, 4 mg/m$^2$, 4.25 mg/m$^2$ or 4.5 mg/m$^2$.

In some embodiments, the method wherein the amount of the compound is administered once daily.

In some embodiments, the method wherein the amount of the compound is administered once daily for at least 1 week.

In some embodiments, the method wherein the amount of the compound is administered once daily for at least 1 month.

In some embodiments, the method wherein the amount of the compound is administered once daily for at least 1 year.

In some embodiments, the method wherein the amount of the compound is administered once daily for a three day period.

In some embodiments, the method wherein the amount of the compound is administered three times per week.

In some embodiments, the method wherein the amount of the compound is administered on three separate days during a seven day period.

In some embodiments, the method wherein the amount of the compound is administered on three separate days during a twenty-one day treatment cycle.

In some embodiments, the method wherein the amount of the compound is administered on three separate days during week 1 of a twenty-one day treatment cycle.

In some embodiments, the method wherein the amount of the compound is administered on days 1, 2 and 3 of a twenty-one day treatment cycle.

In some embodiments, the method wherein the amount of the compound is administered on days 1, 2 and 3 of a twenty-one day treatment cycle and the cycle is repeated one or more times.

In some embodiments, the method wherein the amount of the compound is administered on days 1, 2 and 3 of a twenty-one day treatment cycle and the cycle is repeated one or more times.

In some embodiments, the method wherein the amount of the compound is administered on days 1, 2 and 3 of a twenty-one day treatment cycle and the cycle is repeated two or more times.

In some embodiments, the method wherein the amount of the compound is administered on days 1, 2 and 3 of a twenty-one day treatment cycle and the cycle is repeated three or more times.

In some embodiments, the method wherein the amount of the compound is administered on days 1, 2 and 3 of a twenty-one day treatment cycle and the cycle is repeated four or more times.

In some embodiments, the method wherein the amount of the compound is administered on days 1, 2 and 3 of a twenty-one day treatment cycle and the cycle is repeated five or more times.

In some embodiments, the method wherein the amount of the compound is administered on days 1, 2 and 3 of a twenty-one day treatment cycle and the cycle is repeated six or more times.

In some embodiments, the method wherein the amount of the compound is administered on days 1, 2 and 3 of a twenty-one day treatment cycle and the cycle is repeated between 1 to 10 times.

In some embodiments, the method wherein the amount of the compound is administered once weekly.

In some embodiments, the method wherein the amount of the compound is administered twice weekly.

In some embodiments, the method wherein the amount of the compound is administered once monthly weekly.

In some embodiments, the method wherein of the compound is administered once weekly or twice weekly for 1 to 6 weeks.

In some embodiments, the method wherein the amount of the compound is administered once monthly for 1 to 6 months.

In some embodiments, the method comprising administering to the subject an amount of 0.25 mg to 7.5 mg of the compound.

In some embodiments, the method comprising administering to the subject an amount of 0.25 mg to 4 mg of the compound.

In some embodiments, the method comprising administering to the subject an amount of 0.25 mg to 3 mg of the compound.

In some embodiments, the method comprising administering to the subject an amount of 0.25 mg to 2 mg of the compound.

In some embodiments, the method comprising administering to the subject an amount of 0.25 mg to 1 mg of the compound.

In some embodiments, the method comprising administering to the subject an amount of 1 mg to 5 mg of the compound.

In some embodiments, the method comprising administering to the subject an amount of 1 mg to 4 mg of the compound.

In some embodiments, the method comprising administering to the subject an amount of 1 mg to 3 mg of the compound.

In some embodiments, the method comprising administering to the subject an amount of 1 mg to 2 mg of the compound.

In some embodiments, the method comprising administering to the subject an amount of 4 mg to 7.5 mg of the compound.

In some embodiments, the method comprising administering to the subject an amount of 4 mg to 5 mg of the compound.

In some embodiments, the method comprising administering to the subject an amount of 5 mg to 6 mg of the compound.

In some embodiments, the method comprising administering to the subject an amount of 6 mg to 7 mg of the compound.

In some embodiments, the method comprising administering to the subject an amount of 7 mg to 7.5 mg of the compound.

In some embodiments, the method comprising administering to the subject an amount of 4.8 mg to 7.2 mg of the compound.

In some embodiments, the method comprising administering to the subject an amount of about 0.4 mg, 0.8 mg, 1.3 mg, 2 mg, 2.8 mg or 3.7 mg of the compound.

In some embodiments, the method comprising administering to the subject an amount of about 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg or 7.5 mg of the compound.

In some embodiments of the method, the compound has the structure:

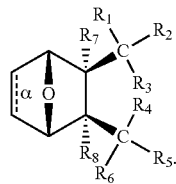

In some embodiments of the method, bond α in the compound is present.

In some embodiments of the method, bond α in the compound is absent.

In some embodiments of the method, the compound wherein
$R_3$ is OH, O⁻, or $OR_9$,
    wherein $R_9$ is alkyl, alkenyl, alkynyl or aryl;
$R_4$ is

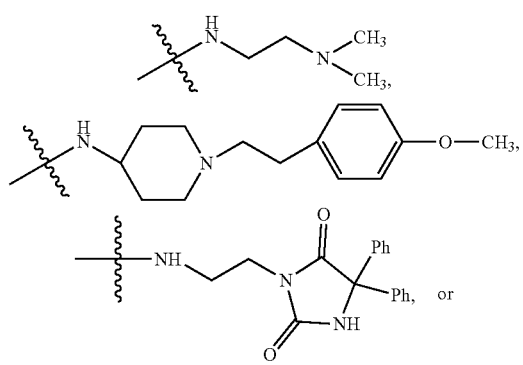

where X is O, S, $NR_{10}$, $N^+HR_{10}$ or $N^+R_{10}R_{10}$,
where each $R_{10}$ is independently H, alkyl, alkenyl, alkynyl, aryl,

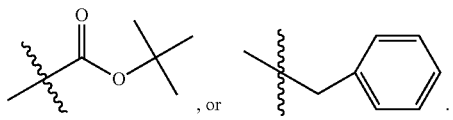

In some embodiments of the method, the compound wherein
$R_3$ is OH, O⁻ or $OR_9$,
    where $R_9$ is H, methyl, ethyl or phenyl In some embodiments of the method, the compound wherein
$R_3$ is OH, O⁻ or $OR_9$,
    where $R_9$ is methyl.

In some embodiments of the method, the compound wherein
$R_4$ is

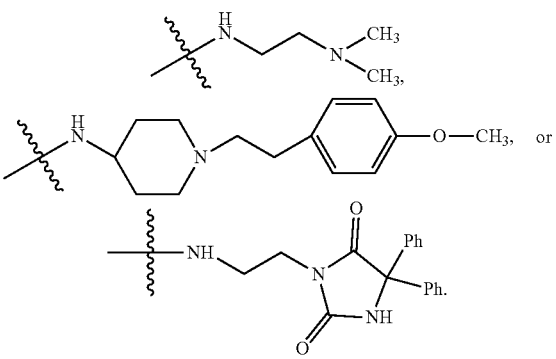

In some embodiments of the method, the compound wherein
$R_4$ is

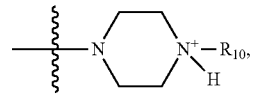

wherein $R_{10}$ is H, alkyl, alkenyl, alkynyl, aryl, or

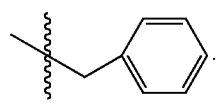

In some embodiments of the method, the compound wherein R$_4$ is

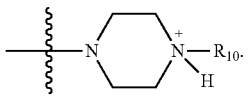

wherein R$_{10}$ is —H, —CH$_3$, —CH$_2$CH$_3$, or

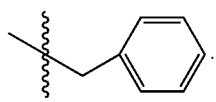 [SMILES: *Cc1ccccc1]

In some embodiments of the method, the compound wherein R$_4$ is

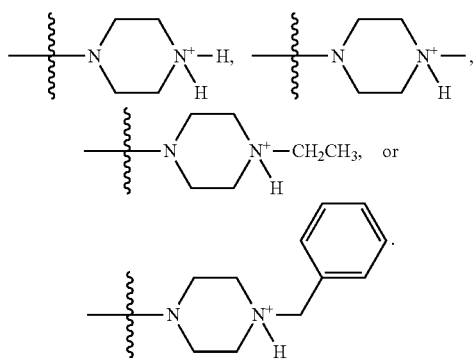

In some embodiments of the method, the compound wherein R$_4$ is

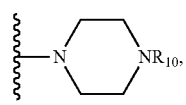

wherein R$_{10}$ is H, alkyl, alkenyl, alkynyl, aryl,

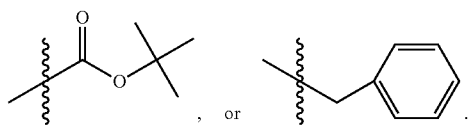

In some embodiments of the method, the compound wherein R$_4$ is

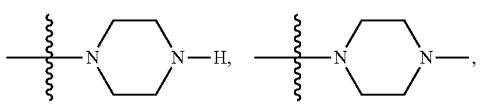

-continued

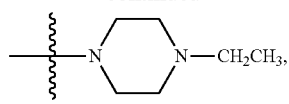

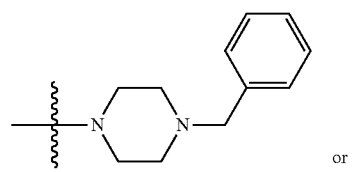

or

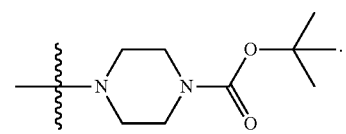

In some embodiments of the method, wherein R$_4$ is

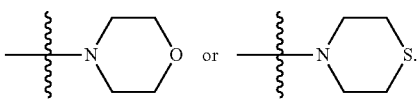 [SMILES: *N1CCOCC1 ; *N1CCSCC1]

In some embodiments of the method, the compound has the structure:

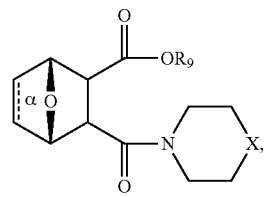

wherein bond α is present or absent;

R$_9$ is present or absent and when present is H, alkyl, alkenyl, alkynyl or phenyl; and X is O, NR$_{10}$, NH$^+$R$_{10}$ or N$^+$R$_{10}$R$_{10}$, where each R$_{10}$ is independently H, alkyl, substituted alkyl, alkenyl, substituted alkenyl, alkynyl, substituted alkynyl, aryl,

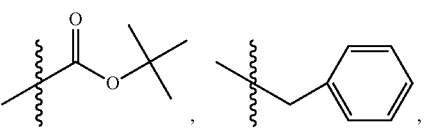

—CH$_2$CN, —CH$_2$CO$_2$R$_{12}$, or —CH$_2$COR$_{12}$, where R$_{12}$ is H or alkyl, or a salt, zwitterion or ester thereof.

In some embodiments of the method, the compound has the structure:

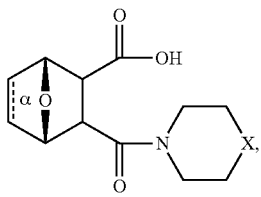

wherein bond α is present or absent;

X is O or NR$_{10}$, where each R$_{10}$ is independently H, alkyl, substituted alkyl, alkenyl, substituted alkenyl, alkynyl, substituted alkynyl, aryl,

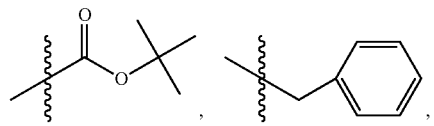

—CH$_2$CN, —CH$_2$CO$_2$R$_{12}$, or —CH$_2$COR$_{12}$, where R$_{12}$ is H or alkyl, or a salt, zwitterion or ester thereof.

In some embodiments of the method, the compound has the structure:

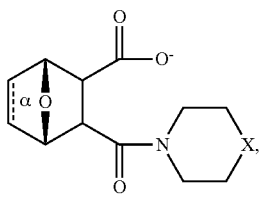

wherein bond α is present or absent;

X is O or NH$^+$R$_{10}$, where R$_{10}$ is H, alkyl, substituted alkyl, alkenyl, substituted alkenyl, alkynyl, substituted alkynyl, aryl,

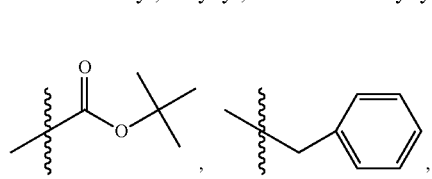

—CH$_2$CN, —CH$_2$CO$_2$R$_{12}$, or —CH$_2$COR$_{12}$, where R$_{12}$ is H or alkyl, or a salt, zwitterion or ester thereof.

In some embodiments of the method, the compound has the structure:

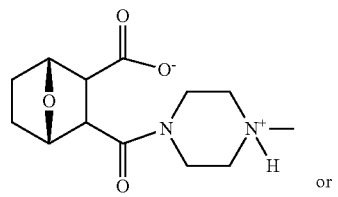

or

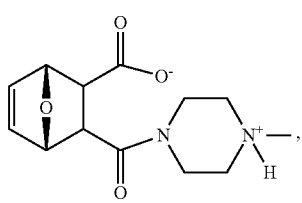

or a salt or ester thereof.

In one embodiment, the compound of the method has the structure:

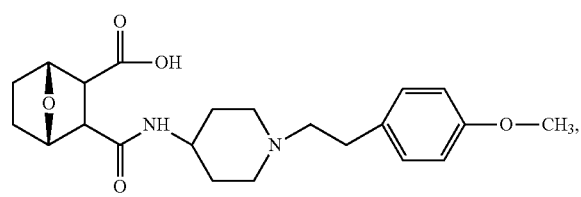

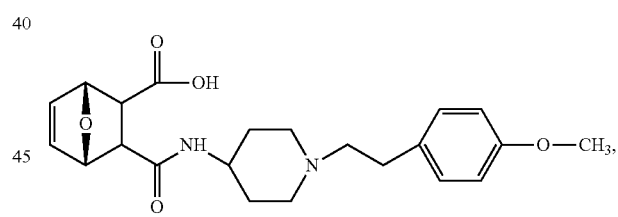

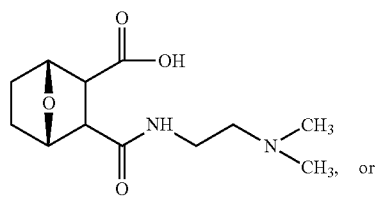

or

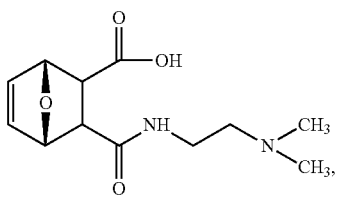

or a salt, zwitterion, or ester thereof.

In one embodiment, the compound of the method has the structure:

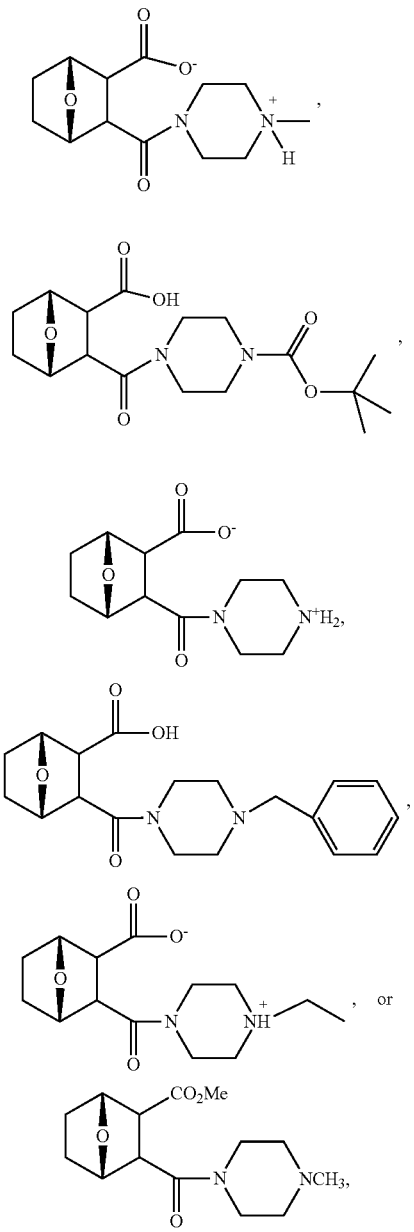

or a salt, zwitterion, or ester thereof.

In one embodiment, the compound of the method has the structure:

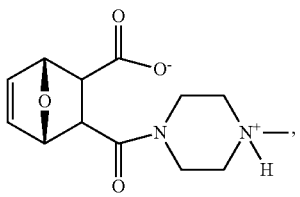

In one embodiment, the compound of the method has the structure:

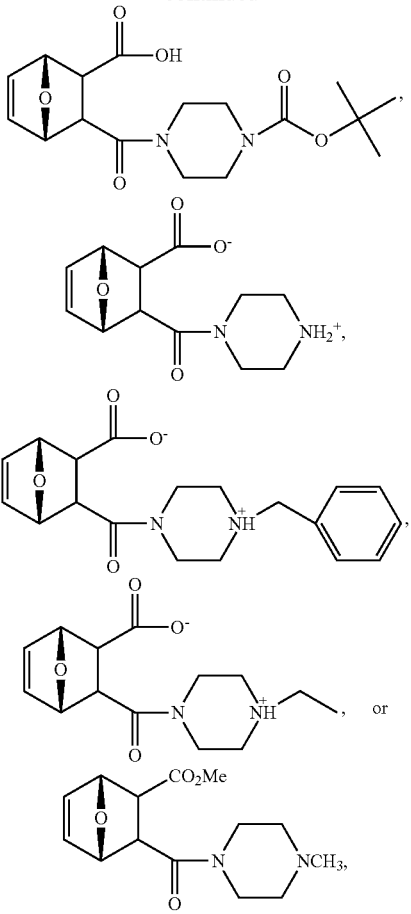

or a salt, zwitterion, or ester thereof.

In one embodiment, the compound of the method has the structure:

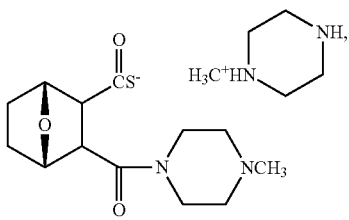

or a salt, zwitterion, or ester thereof.

In one embodiment, the compound of the method has the structure:

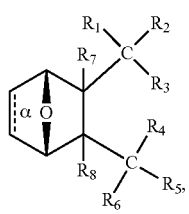

wherein bond α is present or absent;

$R_1$ and $R_2$ together are =O;

$R_3$ and $R_4$ are each different, and each is $O(CH_2)_{1-6}R_9$ or $OR_9$, or

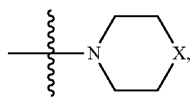

where X is O, S, $NR_{10}$, $N^+HR_{10}$ or $N^+R_{10}R_{10}$, where each $R_9$ is H, alkyl, $C_2$-$C_{12}$ alkyl substituted alkyl, alkenyl, alkynyl, aryl, $(C_6H_5)(CH_2)_{1-6}(CHNHBOC)CO_2H$, $(C_6H_5)(CH_2)_{1-6}(CHNH_2)$ $CO_2H$, $(CH_2)_{1-6}(CHNHBOC)CO_2H$, $(CH_2)_{1-6}(CHNH_2)$ $CO_2H$ or $(CH_2)_{1-6}CCl_3$, where each $R_{10}$ is independently H, alkyl, hydroxyalkyl, $C_2$-$C_{12}$ alkyl, alkenyl, $C_4$-$C_{12}$ alkenyl, alkynyl, aryl,

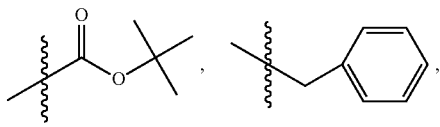

—$CH_2CN$, —$CH_2CO_2R_{11}$, or —$CH_2COR_{11}$, where each $R_{11}$ is independently alkyl, alkenyl or alkynyl, each of which is substituted or unsubstituted, or H;

or $R_3$ and $R_4$ are each different and each is OH or

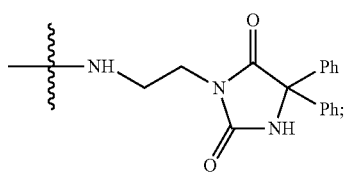 [SMILES: *NCCN1C(=O)NC(c2ccccc2)(c2ccccc2)C1=O]

$R_5$ and $R_6$ taken together are =O;

$R_7$ and $R_8$ are each H; and each occurrence of alkyl, alkenyl, or alkynyl is branched or unbranched, unsubstituted or substituted, or a salt, zwitterion, or ester thereof.

In one embodiment, the compound of the method has the structure:

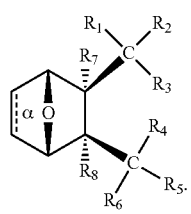

In one embodiment of the method, the bond α is present.
In one embodiment of the method, the bond α is absent.
In one embodiment of the method, $R_3$ is $OR_9$ or $O(CH_2)_{1-6}R_9$, where $R_9$ is aryl, substituted ethyl or substituted phenyl, wherein the substituent is in the para position of the phenyl;

$R_4$ is

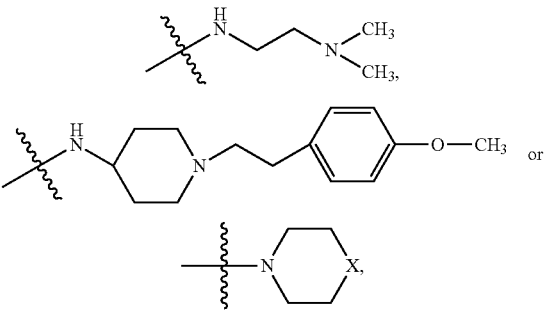

where X is O, S, $NR_{10}$, or $N^+R_{10}R_{10}$.

where each $R_{10}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl,

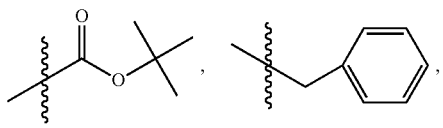

—$CH_2CN$, —$CH_2CO_2R_{11}$, —$CH_2COR_{11}$, where $R_{11}$ is alkyl, alkenyl or alkynyl, each of which is substituted or unsubstituted, or H;

or where $R_3$ is OH and $R_4$ is

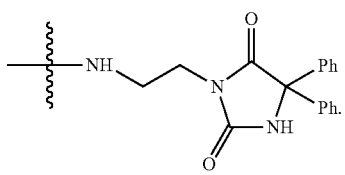 [SMILES: *NCCN1C(=O)NC(c2ccccc2)(c2ccccc2)C1=O]

In one embodiment of the method, $R_4$ is

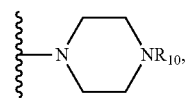

where $R_{10}$ is alkyl or hydroxylalkyl.

In one embodiment of the method, $R_1$ and $R_2$ together are =O;

$R_3$ is $OR_9$ or $O(CH_2)_{1-2}R_9$, where $R_9$ is aryl, substituted ethyl, or substituted phenyl, wherein the substituent is in the para position of the phenyl;

$R_4$ is

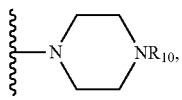

where $R_{10}$ is alkyl or hydroxyl alkyl;
$R_5$ and $R_6$ together are =O; and
$R_7$ and $R_8$ are each independently H.
In one embodiment of the method,
$R_1$ and $R_2$ together are =O;
$R_3$ is $O(CH_2)R_9$, or $OR_9$,
  where $R_9$ is phenyl or $CH_2CCl_3$,

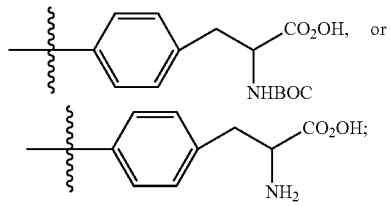

$R_4$ is

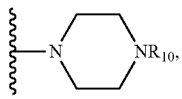

where $R_{10}$ is $CH_3$ or $CH_3CH_2OH$;
$R_5$ and $R_6$ together are =O; and
$R_7$ and $R_8$ are each independently H.
In one embodiment of the method,
$R_3$ is $OR_9$,
  where $R_9$ is $(CH_2)_{1-6}(CHNHBOC)$ $CO_2H$, $(CH_2)_{1-6}(CHNH_2)$ $CO_2H$, or $(CH_2)_{1-6}CCl_3$.
In one embodiment of the method,
$R_9$ is $CH_2(CHNHBOC)CO_2H$, $CH_2(CHNH_2)CO_2H$, or $CH_2CCl_3$.
In one embodiment of the method,
$R_9$ is $(C_6H_5)(CH_2)_{1-6}(CHNHBOC)$ $CO_2H$ or $(C_6H_5)(CH_2)_{1-6}(CHNH_2)CO_2H$.
In one embodiment of the method,
$R_9$ is $(C_6H_5)(CH_2)(CHNHBOC)CO_2H$ or $(C_6H_5)(CH_2)(CHNH_2)CO_2H$.
In one embodiment of the method,
$R_3$ is $O(CH_2)_{1-6}R_9$ or $O(CH_2)R_9$,
  where $R_9$ is phenyl.
In one embodiment of the method,
$R_3$ is OH and $R_4$ is

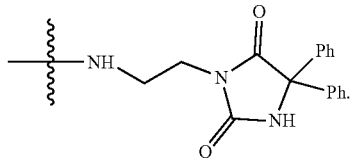 [SMILES: *NCCN1C(=O)NC(c2ccccc2)(c2ccccc2)C1=O]

In one embodiment of the method,
$R_4$ is

wherein $R_{10}$ is alkyl or hydroxyalkyl.
In one embodiment of the method, $R_{11}$ is $—CH_2CH_2OH$ or $—CH_3$.
In one embodiment of the method, the compound has the structure:

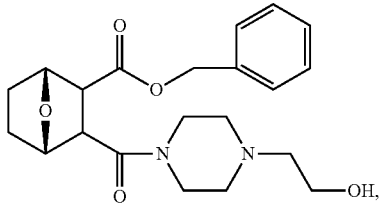

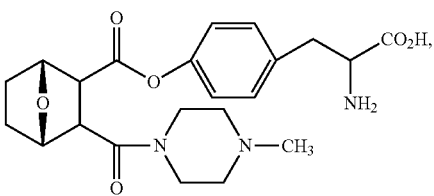

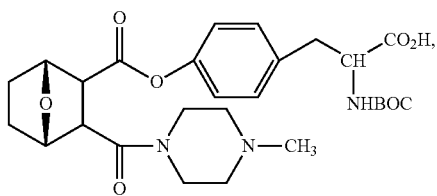

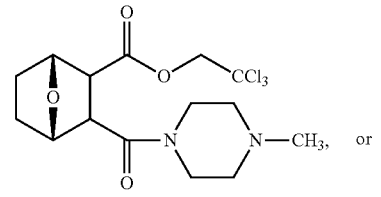

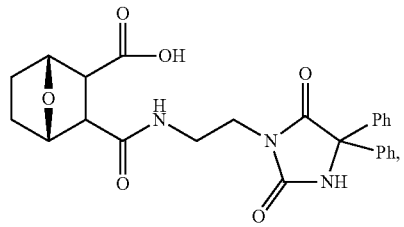

or a salt, zwitterion, or ester thereof.

In one embodiment of the method, the compound has the structure:

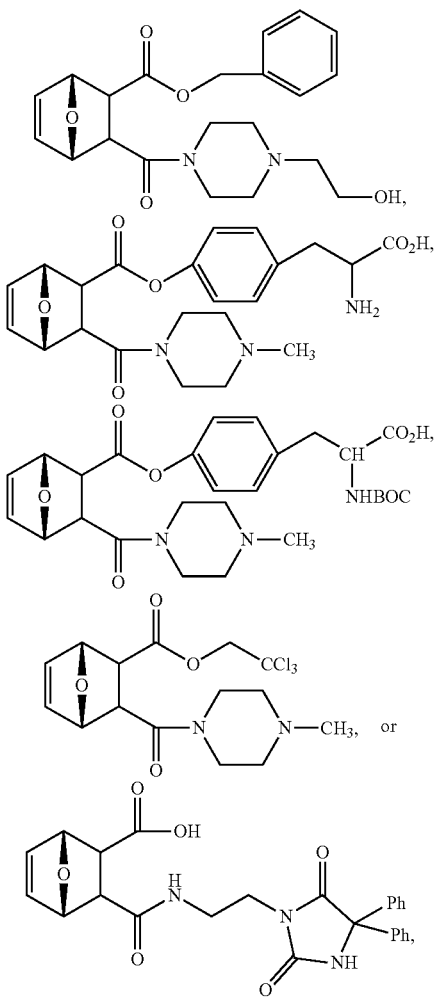

or a salt, zwitterion, or ester thereof.

The present invention also provides a package comprising:
a) a pharmaceutical composition comprising an amount of a phosphatase inhibitor of the present application and a pharmaceutically acceptable carrier; and
b) instructions for use of the pharmaceutical composition to treat a subject afflicted with a depressive or stress disorder.

The present invention further provides a pharmaceutical composition comprising an amount of a phosphatase inhibitor of the present application for use in treating a subject afflicted with a depressive or stress disorder.

The present inventions also provides a therapeutic package for dispensing to, or for use in dispensing to, a subject afflicted with a depressive or stress disorder, which comprises:
a) one or more unit doses, each such unit dose comprising a phosphatase inhibitor of the present application; and
b) a finished pharmaceutical container therefor, said container containing said unit dose or unit doses, said container further containing or comprising labeling directing the use of said package in the treatment of said subject.

The analogs of LB-100 disclosed herein have analogous activity to LB-100 and behave similarly in the assays disclosed herein.

The present invention provides a pharmaceutical composition comprising a compound of the present invention for use in treating a depressive or stress disorder.

In some embodiments, the pharmaceutical composition wherein the pharmaceutically acceptable carrier comprises a liposome.

In some embodiments, the pharmaceutical composition wherein the compound is contained in a liposome or microsphere.

In some embodiments of any of the above methods or uses, the subject is a human. In some embodiments of any of the above methods or uses, the subject is an adult patient, pediatric patient, male patient and/or female patient.

In some embodiments of any of the above methods or uses, the compound is orally administered to the subject.

In one embodiment, the subject afflicted with the depressive or stress disorder has been affirmatively diagnosed to have the condition. For example, a patient afflicted with PTSD means a patient who has been affirmatively diagnosed to have PTSD. The diagnosis of the disorder can be effected using any of the appropriate methods known in the art. For example, PTSD can be diagnosed by psychological evaluation and/or by meeting the criteria in the Diagnostic and Statistical Manual of Mental Disorders (DSM-5), published by the American Psychiatric Association.

In an embodiment of the present invention the method includes the step of identifying or determining whether the subject is afflicted with the depressive or stress disorder.

The compounds used in the method of the present invention are protein phosphatase 2A (PP2A) inhibitors. Methods of preparation may be found in Lu et al., 2009a-b; U.S. Pat. No. 7,998,957 B2; and U.S. Pat. No. 8,426,444 B2. Compound LB-100 is an inhibitor of PP2A in vitro in human cancer cells and in xenografts of human tumor cells in mice when given parenterally in mice. LB-100 inhibits the growth of cancer cells in mouse model systems.

In one embodiment of any of the above methods, the method consisting essentially of administering the compound.

As used herein, a "symptom" associated with the depressive or stress disorder includes any clinical or laboratory manifestation associated with depressive or stress disorders and is not limited to what the subject can feel or observe.

As used herein, "treatment of the diseases" or "treating", e.g. of reperfusion injury, encompasses inducing prevention, inhibition, regression, or stasis of the disease or a symptom or condition associated with the disease.

As used herein, "inhibition" of disease progression or disease complication in a subject means preventing or reducing the disease progression and/or disease complication in the subject.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{20}$ alkyl, $C_2$-$C_{20}$ alkyl, $C_3$-$C_{20}$ alkyl, $C_4$-$C_{20}$ alkyl and so on. An embodiment can be $C_1$-$C_{30}$ alkyl, $C_2$-$C_{30}$ alkyl, $C_3$-$C_{30}$ alkyl, $C_4$-$C_{30}$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl, $C_3$-$C_{12}$ alkenyl, $C_2$-$C_{20}$ alkenyl, $C_3$-$C_{20}$ alkenyl, $C_2$-$C_{30}$ alkenyl, or $C_3$-$C_{30}$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_{12}$ alkynyl, $C_2$-$C_{20}$ alkynyl, $C_3$-$C_{20}$ alkynyl, $C_2$-$C_{30}$ alkynyl, or $C_3$-$C_{30}$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynl, or aryl groups as hereinabove defined.

Each occurrence of alkyl, alkenyl, or alkynyl is branched or unbranched, unsubstituted or substituted.

The alkyl, alkenyl, alkynyl, and aryl substituents may be unsubstituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprolactones and PLGA's).

Other injectable drug delivery systems include solutions, suspensions, gels. Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

The compounds used in the method of the present invention may be in a salt form. As used herein, a "salt" is a salt of the instant compounds which has been modified by making acid or base salts of the compounds. In the case of compounds used to treat an infection or disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The present invention includes esters or pharmaceutically acceptable esters of the compounds of the present method. The term "ester" includes, but is not limited to, a compound containing the R—CO—OR' group. The "R—CO—O" portion may be derived from the parent compound of the present invention. The "R'" portion includes, but is not limited to, alkyl, alkenyl, alkynyl, heteroalkyl, aryl, and carboxy alkyl groups.

The present invention includes pharmaceutically acceptable prodrug esters of the compounds of the present method. Pharmaceutically acceptable prodrug esters of the compounds of the present invention are ester derivatives which are convertible by solvolysis or under physiological conditions to the free carboxylic acids of the parent compound. An example of a pro-drug is an alkly ester which is cleaved in vivo to yield the compound of interest.

The compound, or salt, zwitterion, or ester thereof, is optionally provided in a pharmaceutically acceptable composition including the appropriate pharmaceutically acceptable carriers.

As used herein, an "amount" or "dose" of an agent measured in milligrams refers to the milligrams of agent present in a drug product, regardless of the form of the drug product.

The National Institutes of Health (NIH) provides a table of Equivalent Surface Area Dosage Conversion Factors below (Table 1) which provides conversion factors that account for surface area to weight ratios between species.

TABLE 1

Equivalent Surface Area Dosage Conversion Factors

|  |  | To | | | | |
|---|---|---|---|---|---|---|
|  |  | Mouse 20 g | Rat 150 g | Monkey 3 kg | Dog 8 kg | Man 60 kg |
| From | Mouse | 1 | ½ | ¼ | ⅙ | 1/12 |
|  | Rat | 2 | 1 | ½ | ¼ | 1/7 |
|  | Monkey | 4 | 2 | 1 | ⅗ | ⅓ |
|  | Dog | 6 | 4 | 1⅔ | 1 | ½ |
|  | Man | 12 | 7 | 3 | 2 | 1 |

As used herein, the term "therapeutically effective amount" or "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

Where a range is given in the specification it is understood that the range includes all integers and 0.1 units within that range, and any sub-range thereof. For example, a range of 77 to 90% is a disclosure of 77, 78, 79, 80, and 81% etc.

As used herein, "about" with regard to a stated number encompasses a range of +one percent to −one percent of the stated value. By way of example, about 100 mg/kg therefore includes 99, 99.1, 99.2, 99.3, 99.4, 99.5, 99.6, 99.7, 99.8, 99.9, 100, 100.1, 100.2, 100.3, 100.4, 100.5, 100.6, 100.7, 100.8, 100.9 and 101 mg/kg. Accordingly, about 100 mg/kg includes, in an embodiment, 100 mg/kg.

It is understood that where a parameter range is provided, all integers within that range, and tenths thereof, are also provided by the invention. For example, "0.2-5 mg/m$^2$" is a disclosure of 0.2 mg/m$^2$, 0.3 mg/m$^2$, 0.4 mg/m$^2$, 0.5 mg/m$^2$, 0.6 mg/m$^2$ etc. up to 5.0 mg/m$^2$.

All combinations of the various elements described herein are within the scope of the invention.

For the foregoing embodiments, each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Material and Methods

Experimental Subjects and Inescapable Shock Procedure

C57Bl/6J mice wild-type males of 4-7 weeks were used in accordance with the guidelines of the French Agriculture and Forestry Ministry for handling animal. They were housed at groups of 4-6 per cage with water and food ad libitum available.

The inescapable shock procedure was previously described in Stamatakis and Stuber 2012. Briefly, we placed mice into standard mouse behavioral chambers (Imetronics) equipped with a metal grid floor. We let them to habituate at the new environment for 5 m. In a 20 m session animals received either 19 or 0 unpredictable foot shocks (1 mA, 500 ms) with an interstimulus interval of 30, 60 or 90 s. We anesthetized mice for patch-clamp electrophysiology 1 h, 24 h, 7 d, 14 d or 30 d after the session ended.

Electrophysiology

Animals were anesthetized with Ketamine/Xylazine (50 mg/10 mg Kg-1 i.p.; Sigma-Aldrich, France). The preparation of LHb-containing brain slices was done in bubbled ice-cold 95% $O_2$/5% $CO_2$-equilibrated solution containing (in mM): cholineCl 110; glucose 25; $NaHCO_3$ 25; $MgCl_2$ 7; ascorbic acid 11.6; Na+-pyruvate 3.1; KCl 2.5; $NaH2PO4$ 1.25; $CaCl2$ 0.5. Sagittal slices (250 µm) were stored at room temperature in 95% $O_2$/5% $CO_2$-equilibrated artificial cerebrospinal fluid (ACSF) containing (in mM): NaCl 124; $NaHCO_3$ 26.2; glucose 11; KCl 2.5; $CaCl2$ 2.5; $MgCl2$ 1.3; $NaH_2PO_4$ 1. Recordings (flow rate of 2.5 ml/min) were made under an Olympus-BX51 microscope (Olympus, France) at 32° C. Currents were amplified, filtered at 5 kHz and digitized at 20 kHz. Access resistance was monitored by a step of −4 mV (0.1 Hz). Experiments were discarded if the access resistance increased more than 20%.

The internal solution to measure GABAB-GIRK currents and neuronal excitability contained 140 mM potassium gluconate, 4 mM NaCl, 2 mM $MgCl_2$, 1.1 mM EGTA, 5 mM HEPES, 2 mM $Na_2ATP$, 5 mM sodium creatine phosphate, and 0.6 mM $Na_3GTP$ (pH 7.3), with KOH. When we measured the synaptic inhibitory or excitatory release the internal solution contained (in mM): CsCl 130; NaCl 4; $MgCl_2$ 2; EGTA 1.1; HEPES 5; $Na_2ATP$ 2; Na+-creatine-phosphate 5; $Na_3GTP$ 0.6, and spermine 0.1. The liquid junction potential was −3 mV. For cell-attached recordings the internal solution consisted in ACSF.

Cell-attached recordings in ACSF were performed in GΩ seal with a Vc=0 and Hc=0. Whole-cell voltage clamp recordings were achieved to measure GABAB-GIR currents in presence of Bicuculine (10 µM), NBQX (20 µM) and AP5 (50 µM). For agonist-induced currents, changes in holding currents in response to bath application of baclofen were measured (at −50 mV every 5 s). GABAB-GIRK currents were confirmed by antagonism with either 10 µM of CGP54626, a specific GABAB antagonist or 1 mM $Ba^2$, a selective inhibitor of inward rectifiers. For the GTPγS experiment, 100 µM of GTPγS was added to the internal solution in place of $Na_3GTP$.

For the Okadaic acid (OA) and the CaMKII inhibitor KN93 experiments, respectively 100 nM of OA or 10 µM of KN93 were added in the internal solution. For the PP2A inhibitor LB100 experiments, LB100 (0.1 µM) was applied in the bath. Miniature excitatory postsynaptic currents (mEPSCs) were recorded in voltage-clamp mode at −60 mV in presence of bicuculine (10 µM) and TTX (1 µM). Miniature inhibitory postsynaptic currents (mIPSCs) were recorded (−60 mV) in presence of NBQX (20 µM) and TTX (1 µM). EPSCs and IPSCs were evoked through an ACSF filled monopolar glass electrode placed 200 µm from the recording site in the stria medullaris. AMPA:NMDA ratios of evoked-EPSC were obtained by AMPA-EPSC −60 mV/NMDA-EPSCs at +40 mV. Rectification Index (RI) was computed by AMPAEPSC-60/AMPA-EPSC+40. For the experiments in which high-frequency stimulation trains were used to determine presynaptic release probability, QX314 (5 mM) was included in the internal solution to prevent the generation of sodium spikes. Current-clamp experiments, were performed by a series of current steps (negative to positive) injected to induce action potentials (5-10 pA injection current per step, 800 ms).

In Vivo LB100 Treatment

For LB treatment experiments, mice were injected with LB (1.5 mg/Kg i.p.) or saline 6-8 hours after the FsE. The effects of the treatment on the LHb excitability and GABAB-GIRKs currents as well as the behavioural assay were assessed at day 1 or 7. For both electrophysiology and behaviour once treated the animal were housed in groups of 4-6 and let undisturbed until the day of the test.

LB100 Local Injections

Animals were anesthetized with Ketamine (90 mg/kg)/Xylazine (15 mg/kg i.p.)(Sigma-Aldrich, France) 6-8 hours after the shock protocol and before bilateral injection with LB100 (1 µM) in the LHb: A-P: −1.7; M-L: ±0.45; D-V: −3.1. Retrobeads (Lumafluor, Nashville, US) were added for post histological identification of the injection site. Control animals were simply injected with PBS and retrobeads in a final volume of 300-500 nl. Brain slices from mice injected were directly examined under fluorescent microscope. Only animals with correct injections site were included in the analysis. qRT-PCR LHb punches (2 mm diameter, 2 mm thick) were taken from male C57BL/6J mice (4-7 weeks). Quantitative analysis of GIRK1, GIRK2, GIRK3 and GIRK4 mRNA levels was performed.

Quantitative Immunoelectron Microscopy

The subcellular distribution of Girk2 and GABABR1 was measured using preembedding immunoelectron microscopy and quantitative analysis approaches, as previously described (Arora et al 2011).

Other Aversion Induced Protocols

Odor Predator Exposure

Mice were exposed to a predator odor by presenting for 5 min a cotton ball soaked with red fox urine (5 ml Red fox P; Timk's, Safariland Hunting Corp., Trappe, Mass.) placed in a plastic container (holes equipped) in a corner of a transport cage. For the control group instead fox urine we added 5 ml of water. One hour after the procedure, the mice were anesthetized for the vitro recordings.

Restraint Stress

A ventilated 50 ml falcon tube placed at the center of a transport cage was employed to constrain the mice for 1 h (from 9.00 to 10.00 am). Control animals were let undisturbed in a transport cage for the same amount of time. The mice were anesthetized for the vitro recordings, one hour after the procedure.

Behavioral Assays.

All behavioral tests were conducted during the light phase (8:00-19:00), 1 or 7 days after the shock procedure.

Re-exposure to the Context Test

For this experiment mice were re-exposed 24 h after to the chamber where they received (or not) shocks for a total duration of 5 m. Online analysis of the freezing was performed by viewing a video monitor in a room separate from the mice during the test period. Offline analysis was performed by a second observer. Freezing was defined as the absence of visible movement except that required for respiration (fluctuation in the volume of the thorax) (score: 1). Scanning was assessed when the animal showed a sole movement of the head to scan the environment in a defensive position (score: 0.5). The behavior was scored according to a 5-sec instantaneous time-sampling procedure every 25 sec (Fanselow and Bolles 1979). The observer scored the animal as freezing, scanning or active at that instant and then proceeded to the next chamber. After chamber 6, the observer started again with chamber 1. Thus each animal was scored every 5-sec, yielding 10 observations for each mouse for total 5 minutes session. The cumulative score were converted into percent time freezing by dividing the number of freezing-scanning observations by the total number of observations for each mouse.

Forced Swim Test

Forced swim test was conducted under normal light condition as previously described (Meye, Valentinova, Lecca et al 2015). Mice were placed in a cylinder of water (temperature 23-25° C.; 14 cm in diameter, 27 cm in height for mice) for six min. The depth of water was set to prevent animals from touching the bottom with their hind limbs. Animal behavior was videotracked from the top (Viewpoint, France). The latency to the first immobility event and the immobility time of each animal spent during the test was counted online by two independent observer blind of the animal treatments. Immobility was defined as floating or remaining motionless, which means absence of all movement except motions required to maintain the head above the water.

Analysis and Drugs

All drugs were obtained from Abcam (Cambridge, UK), Tocris (Bristol, UK) and Sigma (Lyon, France) and dissolved in water, except for TTX (citric acid 1%). Analysis for the electrophysiology data was performed in blocks depending on the experiment. Online/offline analyses were performed using IGOR-6 (Wavemetrics, US) and Prism (Graphpad, US). Sample size required for the experiment was empirically tested by running pilots experiments in the laboratory. Data distribution was previously tested by the Kolgorov Smirnoff and D'Agostino Pearson. Depending by the distribution parametric or not parametric test were used. Single data points are always plotted. Compiled data are expressed as mean±s.e.m. Significance was set at $p<0.05$ using Student's t-test, one or two-way ANOVA with multiple comparison when applicable. Mann Withney test was used when required.

Example 1. A Single Foot Shock Exposure Produces Depressive-like Behaviors and Increases LBb Neuronal Excitability The LHb mediate different behavioral phenotypes mostly linked to aversive-related conditions (Lecca et al., 2014). Increased excitatory output from the LHb is crucial for driving aversion to external context and avoidance behaviors (Stamatakis and Stuber, 2012). However, whether adaptations occurring in the LHb early after the exposure to an aversive experience are ultimately important for behavioral responses is unknown.

To test this, behavioral consequences upon the exposure to a single session of foot-shocks (FsE), a protocol that if stronger drives acute learned helplessness, were examined (Hammack et al., 2012; Li et al., 2011). C57/BL6J mice were exposed to none or 19 unpredictable foot-shocks in a single 20 minutes session (FIG. 1A)(Stamatakis and Stuber, 2012). Animals were re-exposed to the context 24 hours after the protocol, and as predicted, mice presented a high level of freezing, a behavioral trait typical of fear conditioning (FIG. 1B)(Luthi and Luscher, 2014). The same group of animals was then tested 7 days after the FsE by employing the forced swim test (FST) paradigm to assess depressive-like states (Porsolt et al., 1977). FsE resulted in depressive-like behaviors, with a reduced latency to first immobility and increased total immobility in the FST, indicating that a single exposure to a session of aversive stimuli have important behavioral consequences (FIG. 1C).

Hyperexcitability in the LHb contributes to disorders characterized by depressive-like phenotypes including depression and addiction (Li et al., 2011; Shabel et al., 2014; Stamatakis and Stuber, 2012) (Meye, Valentinova, Lecca et al., 2015). Use of drugs or alcohol produces rewarding effects followed by aversive effects including depression. The LHb has also been implicated in aversive effects caused by drug or alcohol addiction or withdrawal from drug or alcohol addiction (Jhou, T. C. et al. 2013; Meye, F. J. et al. 2015).

It was predicted that the establishment of depressive-like traits after FsE relies, at least in part, to modifications in LHb function. To test this, LHb neurons spontaneous action potentials were measured in cell-attached mode 1 hour after FsE (FIG. 1D).

Figures 1D, 1E, 1F:
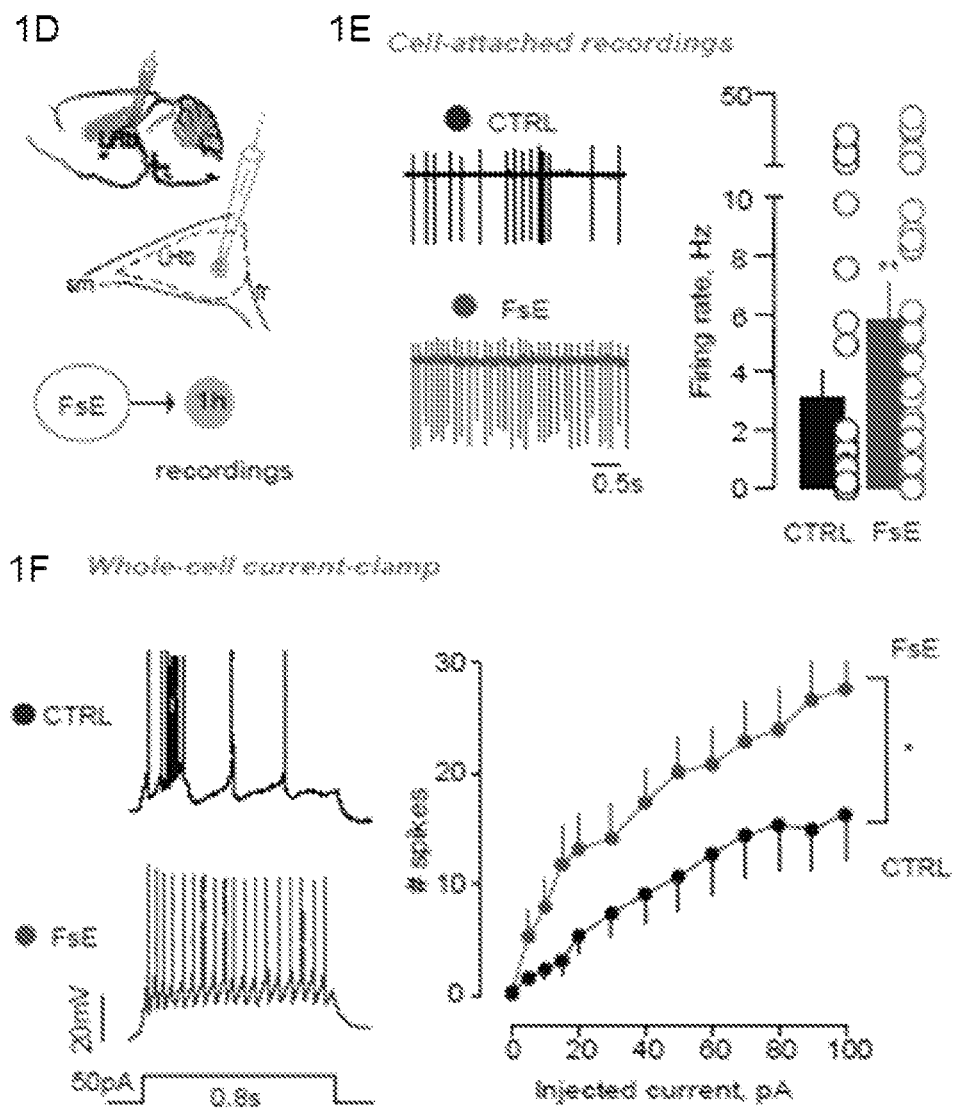
FIG. 1D: FsE-induced depressive-like phenotype and neuronal hyperexcitability in the LHb. Schematic representing a sagittal section of the mouse brain containing the lateral habenula. The dashed line delimitated the area of recordings.
FIG. 1E: FsE-induced depressive-like phenotype and neuronal hyperexcitability in the LHb. FsE increases the spontaneous firing activity in LHb neurons recorded in a cell-attached configuration. The representative traces from two different cells in a CTRL and FsE mice respectively show the higher firing activity in the last condition. The bar graph and plot report the significant increase in the tonic activity in the FsE LHb neuronal population (CTRL vs FsE; n=42 vs 43; 8 vs 8 mice; 3.12±0.92 Hz vs 5.84±1.27 Hz; Mann Whitney test; **p=0.007).
FIG. 1F: FsE-induced depressive-like phenotype and neuronal hyperexcitability in the LHb. Current-clamp sample traces (50 pA injection) and action potentials evoked by current steps (graph on the right), showing the higher excitability recorded in the LHb neurons from FsE animals (CTRL vs FsE; n=12 vs 14; 3 vs 3 mice; two way ANOVA RM F1, 288=4.78, *p=0.03).

It was found that action potentials were more frequent in mice previously exposed to footshock than in controls (FIG. 1E). Cell-attached recording, although non-invasive may result in alterations in the firing rate (Alcami et al., 2012). To rule out potential technical pitfalls, firing activity using whole-cell recording was compared allowing for an alternative assessment of FsE on LHb neurons activity. It was found that that when plotting the number of action potentials in function of progressively larger current injection, LHb neurons in the FsE presented a larger number of action potential (FIG. 1F).

Altogether this indicates that FsE produces depressive-like states in mice as well as hyperexcitability of LHb neurons.

Figure 2A:
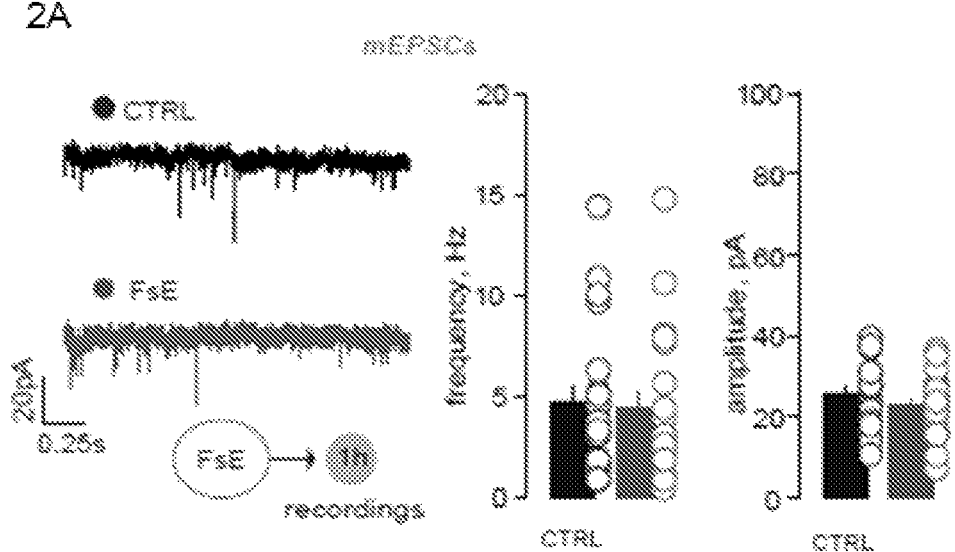
FIG. 2A: FsE does not alter quantal excitatory and inhibitory release but reduces GABAB-GIRK signaling in the LHb. Sample traces, bar graphs and scatters plot showing a similar mEPSCs activity in LHb neurons from CTRL and FsE mice (CTRL vs FsE; n=21 vs 20; 5 vs 5 mice; Frequency, 4.7±0.8 vs 4.5±0.8, Mann Whitney, p=0.7; Amplitude, 25.7±1.8 vs 22.7±1.7, t-test, t39=1.21, p=0.23).

Example 2. Exposure to Aversive Stimuli Depresses GABAB-GIRK Function in the LHb Multiple mechanisms may underlie neuronal excitability including modifications in the balance between excitation/inhibition as well as modifications in ion conductance. To test the underlying cellular mechanisms for cell hyperexcitability in LHb upon FsE, miniature excitatory and inhibitory postsynaptic currents (mEPSCs and mIPSCs) were initially recorded 1 hour after the FsE (FIG. 2A, B). It was found that quantal excitatory and inhibitory synaptic transmission remained unaffected in both frequency and amplitude (FIG. 2A, B). Additionally, no modifications were found in the postsynaptic strength of AMPA or NMDA-mediated transmission nor subunit composition as AMPA/NMDA ratios and rectification index were comparable among experimental groups (Figure S1A). To determine potential FsE-induced modifications in the efficacy of presynaptic neurotransmitter release, evoked transmission was examined placing a stimulating electrode in the stria medullaris. To probe presynaptic function, evoked E/IPSCs were examined with trains at high frequency (10 stimuli delivered at 20 Hz) (Zucker and Regehr, 2002). It was found that at both excitatory and inhibitory trains of synaptic responses were comparable in slices between control and FsE mice (Figure S1B).

GIRK channels hyperpolarize neurons in response to activation of GABAB receptors, thereby providing a fine control of neuronal excitability (Luscher and Slesinger, 2010). Plasticity of GABAB-GIRK signaling is critical for specific behavioral adaptations (Hearing et al., 2013; Padgett et al., 2012). However the functional relevance of GABAB-GIRK signaling in LHb remains understudied. Bath application of a saturating dose of the GABAB-R agonist baclofen (100 μM) evoked an outward current (IBaclofen) that showed little desensitization during continuous drug application (Figure S2A). The outward response was readily reversed by the GABAB-R antagonist CGP54626 (10 μM; Figure S2A & E). Baclofen produced outward responses in a dosedependent manner, with an EC50 of 10.2 μM (Figure S2B). I-Baclofen correlated with a decrease in input resistance (Figure S2C) consistently with activation of K+ conductance. Accordingly, I-Baclofen was abolished in presence of low barium (Ba2+) concentrations (1 mM) indicating that inwardly rectifying K+ channels are likely the effectors of GABAB activation in the LHb (Figure S2D). The LHb of mice were microdissected, and whole tissue real-time PCR was performed. It was found that GIRK1-4 subunits were expressed in the LHb, supporting a functional GABAB-GIRK signaling in the LHb (Figure S2E).

Figure 2B:
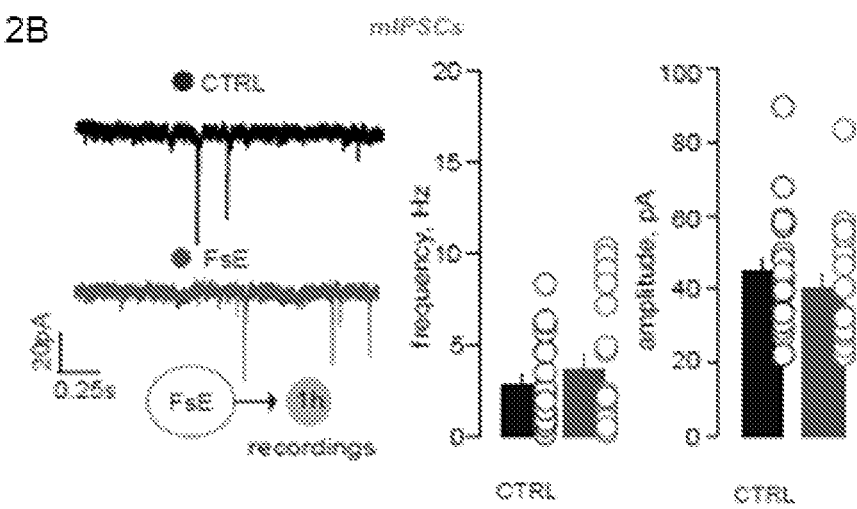
FIG. 2B: FsE does not alter quantal excitatory and inhibitory release but reduces GABAB-GIRK signaling in the LHb. No difference between groups were detected in the frequency and amplitude of mIPSCs (CTRL vs FsE; n=20 vs 20; 5 vs 5 mice; Frequency, 2.8±0.5 vs 3.6±0.7; t-test, t38=0.86, p=0.4; Amplitude, 44.8±3.7 vs 40.4±3.7; t-test, t38=0.82, p=0.4).
Figure 2C:
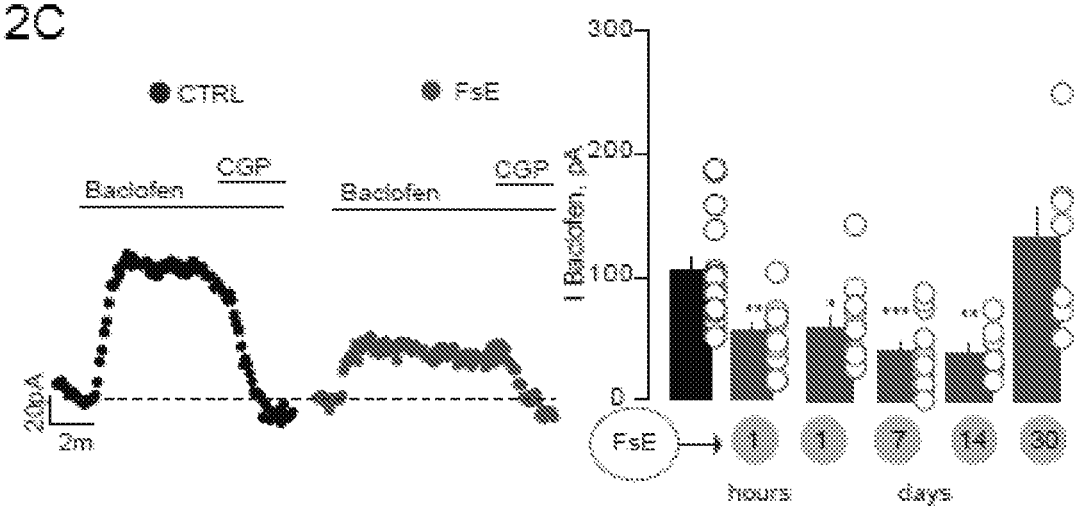
FIG. 2C: FsE does not alter quantal excitatory and inhibitory release but reduces GABAB-GIRK signaling in the LHb. Representative traces of the holding current record in a voltage clamp configuration (Vc=−50 mV) in CTRL and FsE condition. The I-baclofen in the CTRL sample was around 100 pA. Baclofen application (100 μM) in a slice from FsE mouse recorded 1 h after the procedure, showed a reduced response. This attenuation in the peak current resulted completely comparable to CTRL condition 30 days after the exposure (white traces). In all examples I-baclofen was fully reversed by the GABAB antagonist CGP54626. (10 μM). The bar graph and scatter plot reports the long lasting attenuation of GABAB-GIRK $R_S$ currents in the LHb of FsE mice. This plasticity persist for 30 days (CTRL vs FsE 1 hour, 1 day, 7 days, 14 days, 30 days, n=15 vs 12, 12, 11, 8, 7; 5 vs 4, 4, 4, 3, 2; 104.5±11.3 vs 55.4±7.2, 59.8±9.6, 40.1±9.0, 39.6±6.6, 133.0±26.1; one way ANOVA and Dunnet test, F5,64=9.1, *p<0.0001, p<0.001,*p<0.05).
Figure 2D:
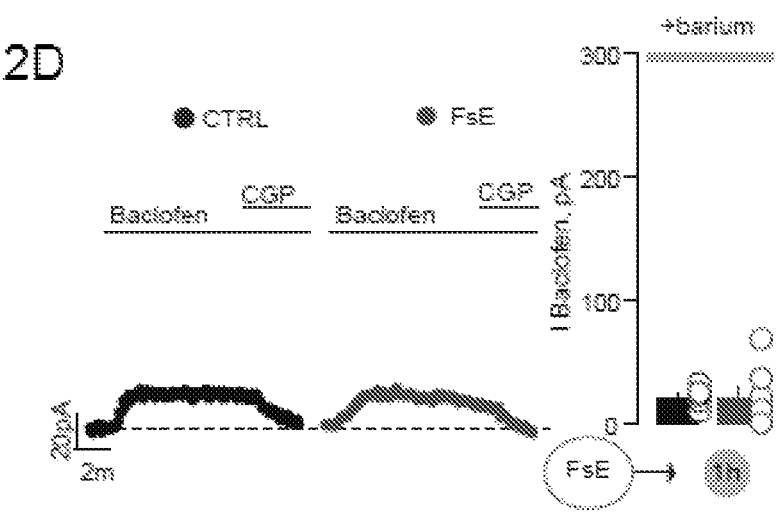
FIG. 2D: FsE does not alter quantal excitatory and inhibitory release but reduces GABAB-GIRK signaling in the LHb. Bar graph showing the absence of difference in the I-baclofen between CTRL and FsE when the recordings were performed in presence of the GIRK blockers barium in the bath (1 mM). The residual current evoked by baclofen, independent by GIRKs is not affected by FsE (CTRL vs FsE, n=5 vs 7, 2 vs 3 mice; 21.3±3.7 vs 21.3±9.1; t test, t10=0.002, p=0.9).

Altogether these results indicate that GABAB-GIRK signaling provide a functionally relevant inhibitory control of LHb neurons activity. To test whether FsE alter the GABAB-GIRK component, whole-cell recordings 1 hour later in LHb neurons were performed, and recorded I-Baclofen in the different experimental groups. I-Baclofen in slices from FsE mice was smaller compared to control mice (FIG. 2C). In order for cellular modifications to be behaviorally relevant, they should not fade off rapidly, providing an important substrate for reorganization of complex neural circuits (Mameli et al., 2009; Chen et al., 2008). To determine the longevity of the FsE-induced adaptations, it was examined whether GABAB-GIRK signaling was reduced after 1, 7, 14, and 30 days following FsE. FsEevoked reduction in I-Baclofen persisted up to 14 days after the paradigm, and it was instead comparable to control values one month after the session (FIG. 2C). The modifications induced after aversive experiences are specific for the GABAB-GIRK signaling. Indeed, the I-Baclofen evoked in the presence of Ba2+ was comparable between control and foot-shock-exposed mice (FIG. 2D). This indicates that solely the GABAB-GIRK, Ba2+-sensitive, component is altered by aversive experience.

Altogether these findings indicate that FsE exposure selectively and persistently modifies GABAB-GIRK signaling in the LHb without altering synaptic transmission onto LHb neurons.

Example 3. GABAB-GIRK Plasticity in the LHb for Generalised Negative Experience

Figures 3A, 3B:
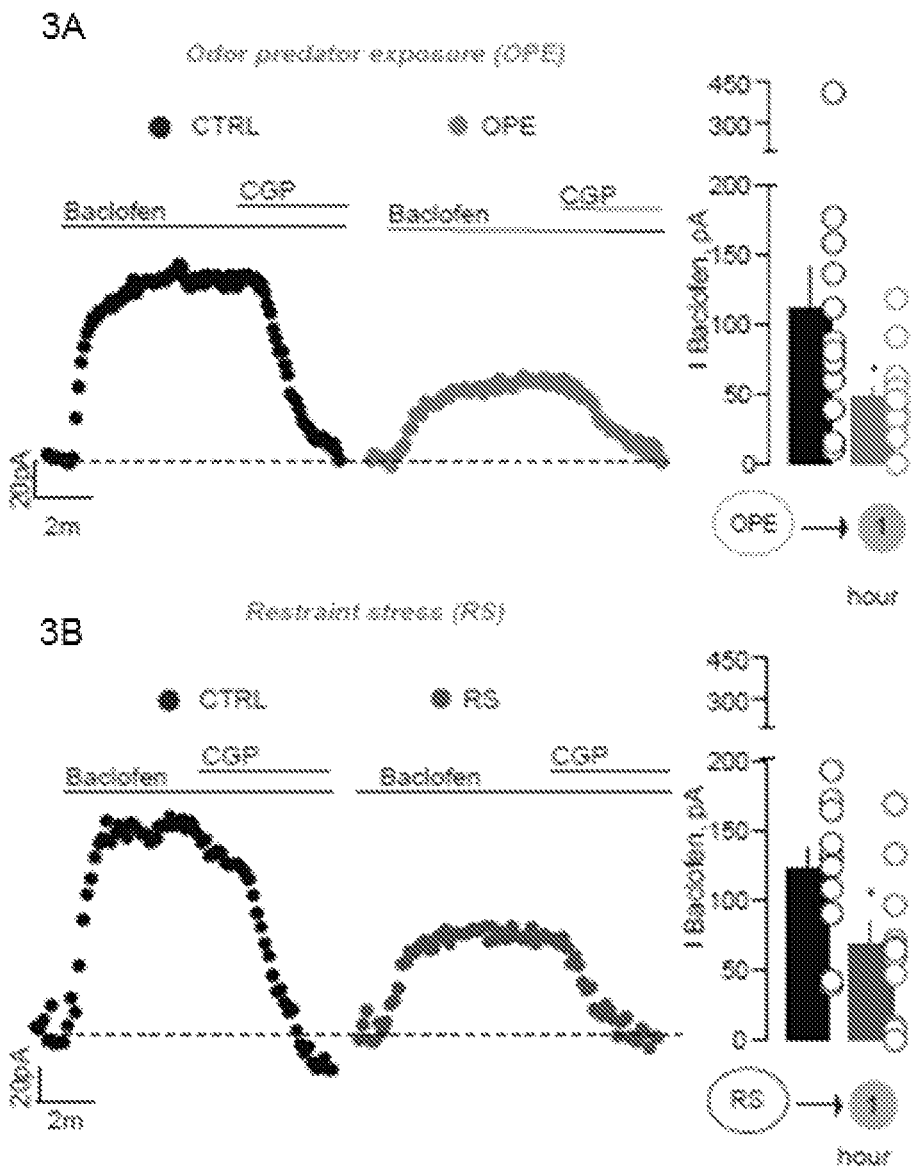
FIG. 3A: Aversive experience of different nature trigger plasticity of GABABGIRK in the LHb. The odor predator exposure paradigm. Sample traces reports the reduction of baclofen-evoked outward current in LHb neurons recorded 1 h after the exposure to fox urine (rightmost trace). The bar graph and scatter plot on the right report the significant reduction of I baclofen compare to the control situation (CTRL vs OPE, n=13 vs 14, 4 vs 4 mice; 110.5±29.1 vs 47.4±7.9; t-test, t25=2.16, *p=0.04).
FIG. 3B: Aversive experience of different nature trigger plasticity of GABABGIRK in the LHb. The restraint stress procedure. The animal was constrained in a plexiglass tube for 1 h. The rightmost trace show a representative recording in a RS mouse 1 h after the procedure. The bar graph and the plots on the right show the significant I-baclofen reduction in RS mice compare to CTRL (CTRL vs FsE, n=11 vs 14, 3 vs 4 mice; 121.7±14.8 vs 68.3±15.3; t-test, t23-2.46, *p=0.02).

Conditions of heightened stress can represent a risk factor for the development of neuropsychiatric disorders spanning to post-traumatic stress disorders to depression (Radley et al., 2011). Heightened stress paradigms, not driven by painful stimuli, but nevertheless capable to trigger avoidance and depressive-like behaviors, were tested to determine if they modified GABAB-GIRK signaling in LHb (Buynitsky and Mostofsky, 2009; Takahashi et al., 2005). The odor predator stress paradigm involves the use of a natural stimulus, as opposed to foot-shock, to provide a condition with heightened stress. Mice were submitted to fox urine for five minutes and slices containing the LHb were prepared 1 hour after exposure. Similarly to FsE mice, I-Baclofen was depressed in animals exposed to the odor predator (FIG. 3A). Furthermore, restraint stress, also used to model depressive-like behaviors in rodents (Hammack et al., 2012), similarly reduced I-Baclofen in LHb neurons (FIG. 3B).

Taken together these findings indicate that the reduction in GABAB-GIRK signaling may represent a common cellular substrate for the encoding of aversive stimuli.

Example 4. FsE-induced GABAB-GIRK Redistribution in the LHb

Figure 4A:
FIG. 4A: FsE depresses GABAB-GIRK signal via their internalization in the LHb. Schematic summarizing the timeline of the electromicroscopy experiment.
Figure 4B:
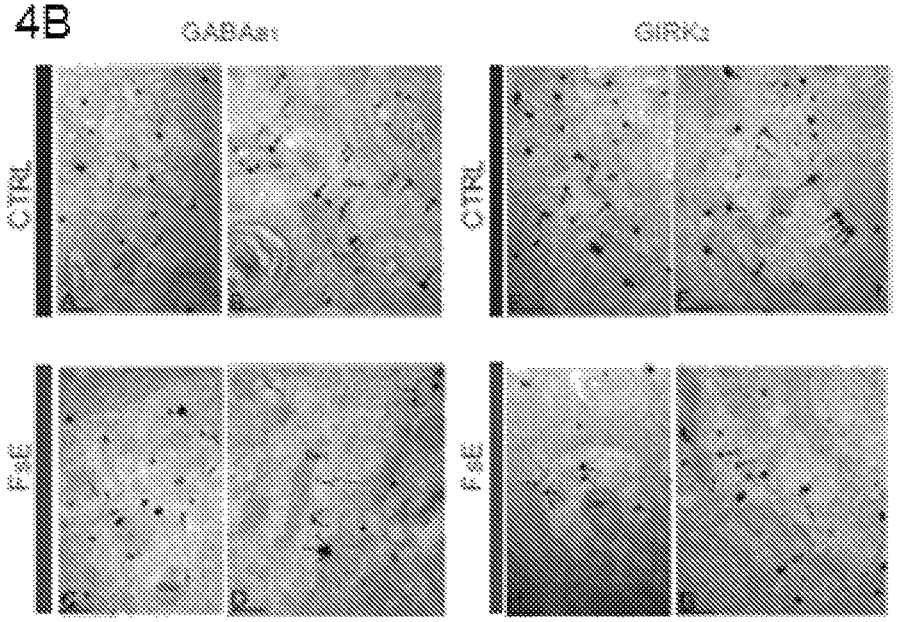
FIG. 4B: FsE depresses GABAB-GIRK signal via their internalization in the LHb. Sample tissue in CTRL (top) and FsE (bottom) for GABAB1 (left) and GIRK2 (right).
Figure 4C:
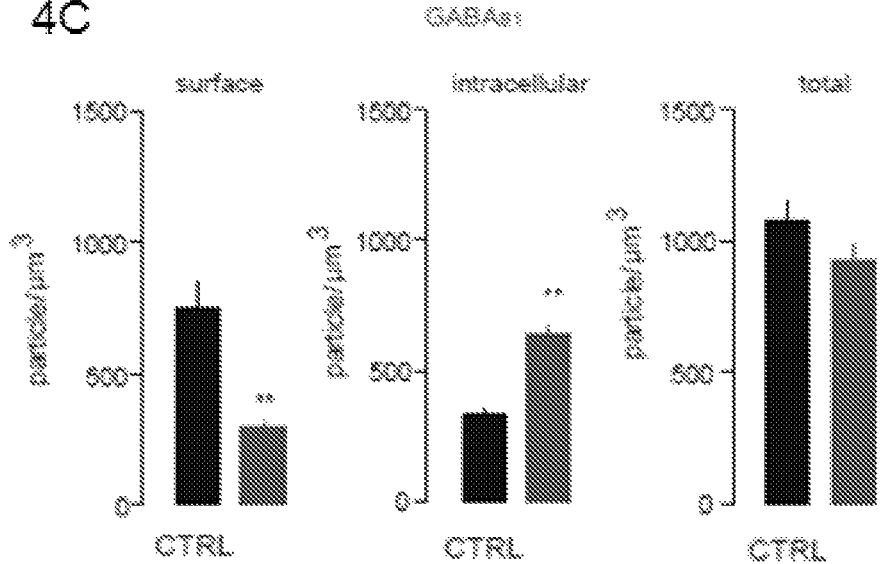
FIG. 4C: FsE depresses GABAB-GIRK signal via their internalization in the LHb. Bar graphs showing that FsE decreases the distribution of GABAB1 at the surface (left), increasing its availability at the intracellular compartment (middle) without affects the total amount (right).

Mechanistically, the reduction of GABAB-GIRK function upon aversive experience may occur via alternative mechanisms including modifications in G protein coupling (Labouebe et al., 2007), scaffolding protein adaptations (Tiao et al., 2008) or internalization of the receptors or receptor/effector complex (Hearing et al., 2013; Padgett et al., 2012). To test the latter scenario, quantitative immuno-electron microscopy was employed to compare the subcellular distribution of GABAB1 and GIRK2 in the LHb in control and FsE mice (FIG. 4A, B). It was found that no global changes in the total GABAB1 and GIRK2 immunolabeling between different experimental groups occurred one hour after FsE (FIG. 4C, D). Membrane GABAB1 and GIRK2 were mainly located at extrasynaptic sites (FIG. 4B). FsE led to a significant reduction in membrane immunolabeling of both GABAB1 and GIRKs, with a corresponding increase in their intracellular labeling (FIG. 4C, D). These finding supports a scenario in which GABAB-Rs and GIRKs traffic out the plasma membrane as a macrocomplex (Boyer et al., 2009; Padgett et al., 2012).

Figures 4D, 4E:
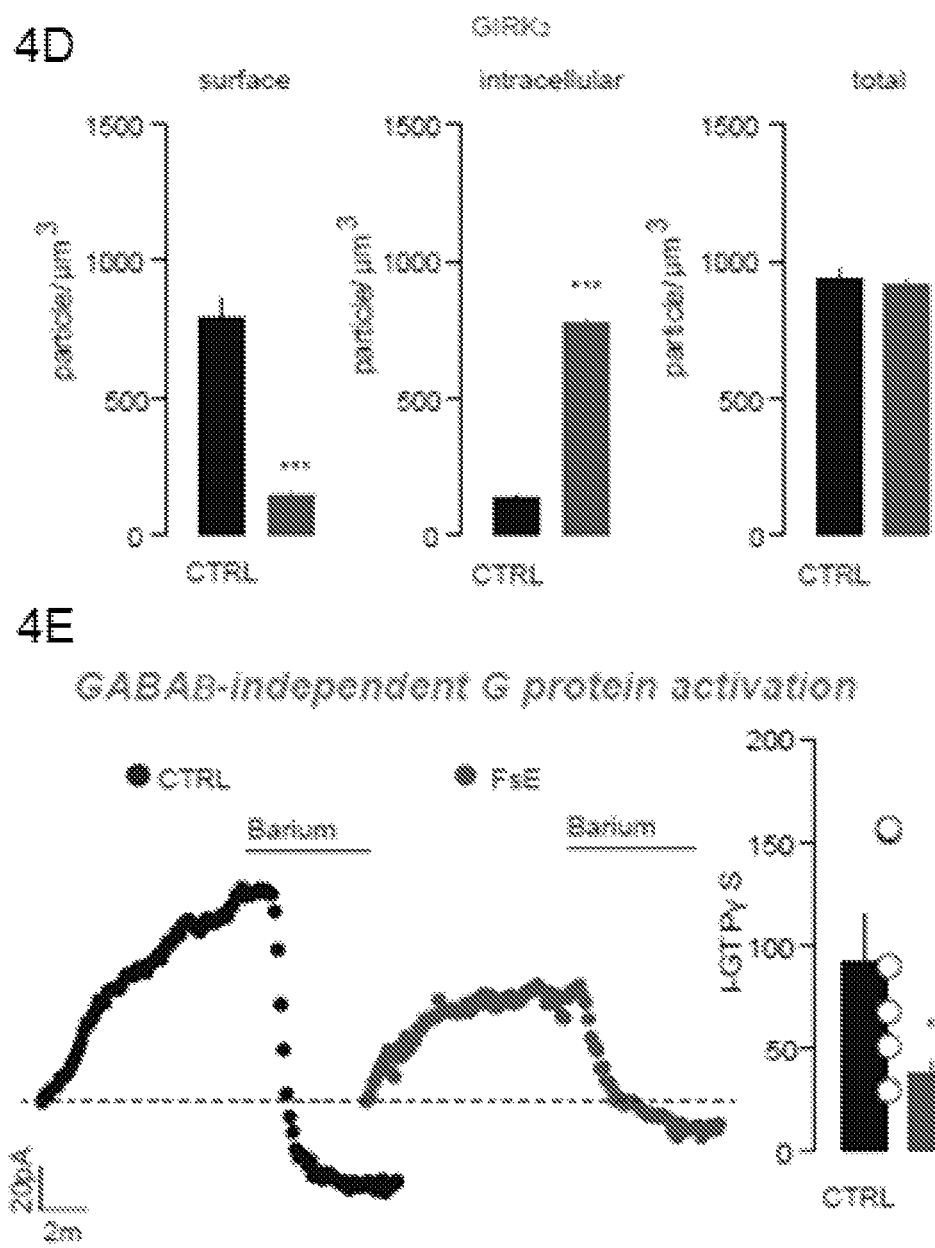
FIG. 4D: FsE depresses GABAB-GIRK signal via their internalization in the LHb. GIRK2 Rs are strongly internalized after FsE. Similarly to the GABAB1 the total amount of GIRK2 Rs is not changed.
FIG. 4E: FsE depresses GABAB-GIRK signal via their internalization in the LHb. Sample traces and bar graph with plots show the G-protein β and γ subunits activation through the GTPγS in the internal solution (100 μM) evoking a $Ba^{2+}$-sensitive outward current (1 mM). In line with EM results, independently by GABAB activation, the currents induced by GTPγS resulted reduced in FsE mice (CTRL vs FsE; n=6 vs 6; 3 vs 3 mice; 92.55±21.83 pA vs 38.00±5.27 pA; t-test, t10=2.43, *p=0.03).

To further assess a reduction in the functional expression of GIRK channels, the effect of intracellular GTPγS was examined. GTPγS is a non-hydrolysable form of guanosine triphosphate (GTP) that allows bypassing GPCR activation and constitutively activate GIRK channels via Gb/g-dependent mechanisms (Logothetis et al., 1987). In light of our immunogold labeling, it was predicted that the intracellular dialysis of GTPγS would elicit smaller outward currents in LHb neurons from FsE mice compared to animals of the control group. In control neurons, intrapatch dialysis of GTPγS (100 μM) led to slow activation of a large outward K+ current sensitive to extracellular $Ba^2$, indicative of GIRK channels activation (FIG. 4E). LHb neurons from slices of FsE mice showed reduced GTPγS-induced Ba2+-sensitive currents (FIG. 4E). These results suggest that, in LHb neurons, FsE diminishes the functional membrane expression of GIRK channels coupled to GABAB receptors.

Example 5. PP2A Activity in LHb Gates FsE-Evoked GABAB-GIRK Internalisation

Figures 5A, 5B:
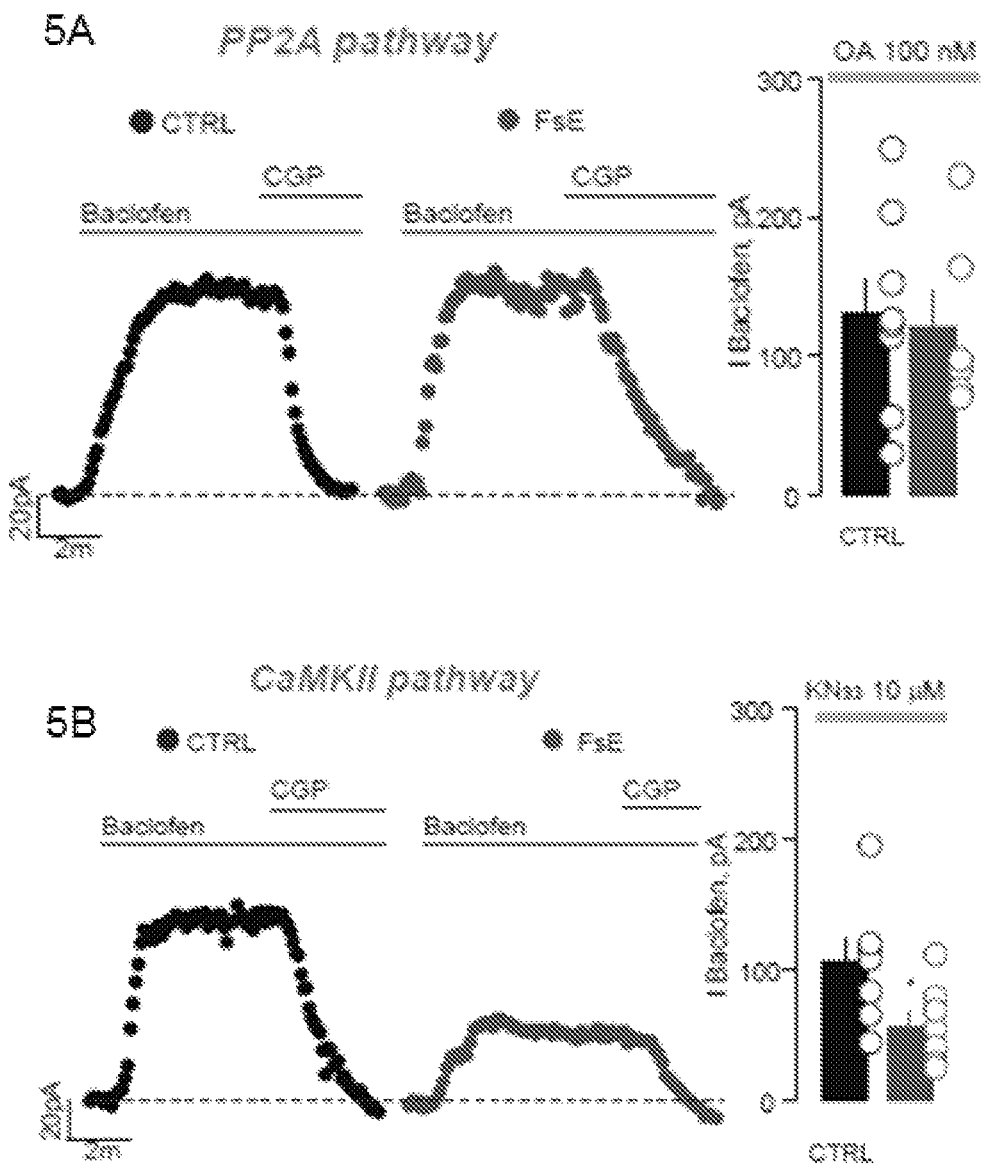
FIG. 5A: PP2A inhibition normalizes GABAB-GIRK function in the LHb after FsE. Sample traces recorded in LHb neurons from CTRL and FsE in presence of the PP2A/PP1 inhibitor Okadaic Acid (100 nM) in the internal solution. Bar graph and scatter plot reporting no difference between groups on the I-baclofen current (CTRL vs FsE; n=8 vs 6, 3 vs 2 mice; 130.7±25.25 pA vs 120.4±25.61 pA; test, t12=0.28, p=0.78).
FIG. 5B: PP2A inhibition normalizes GABAB-GIRK function in the LHb after FsE. CaMKII inhibitor KN93 (10 μM) in the internal solution does not affect the FsE induced reduction of GABAB-GIRK currents. Representative traces and bar graph with scatter plot were shown (CTRL vs FsE; n=7 vs 8, 2 vs 3 mice; 106.3±18.37 pA vs 57.810.38 pA; t-test, t13=2.37, *p<0.03).

The phosphorylation of specific serine residues on the B1 and B2 subunits of the GABAB receptors is determinant to control GABAB-GIRK complex function (Guetg et al., 2010; Terunuma et al., 2010). Specifically, the dephosphorylation of serine 783 (S783) in the GABAB2 is associated with pharmacological and drug-driven reduction in GABAB receptors surface expression in neurons (Padgett et al., 2012; Terunuma et al., 2010). This process relies on the increased activity of protein phosphatase 2A, which constitutively maintains low GABAB-GIRK signaling (PP2A; (Hearing et al., 2013; Padgett et al., 2012; Terunuma et al., 2010)). Hence, FsE may enhance PP2A activity in LHb neurons, promoting the sustained intracellular localization of GABABGIRK complexes. To test this, the effect of acute intracellular inhibition of PP1/PP2A phosphatases was examined by postsynaptic dialysis of okadaic acid through the patch pipette (OA; 100 nM). In control mice and in presence of OA, I-Baclofen was comparable to naïve condition indicating that PP1/PP2A activity does not provide substantial control of GABABR-GIRKs signaling at baseline (FIG. 5A). In contrast, in FsE mice intracellular dialysis of OA led to I-Baclofen amplitudes comparable to control mice (FIG. 5A). This suggests that in the LHb, OA dialysis, and therefore PP1/PP2A inhibition, promptly restore GABAB-GIRK signaling after FsE.

An alternative pathway controlling GABAB surface is the CaMKII-mediated phosphorylation at S867 of GABAB1 (Guetg et al., 2010). To assess a potential involvement of CaMKII in FsE-evoked GABAB-GIRK reduction, the effect of the CaMKII inhibitor, KN93 (10 µM), was examined. Similarly to OA, the intracellular dialysis of KN93 did not affect I-Baclofen at baseline. In contrast, KN93 failed to recover I-Baclofen in slices from FsE mice, as currents were significantly smaller in the FsE group (FIG. 5B). These results suggest a crucial role of PP1/PP2A activity for a constitutive maintenance of internalized GABABRs and GIRKs. The use of OA to inhibit phosphatases activity is however limited to its intracellular use, as it lacks membrane permeability properties. Recent advances in drug development and pharmacotherapy has targeted PP2A activity. Newly developed molecules have been generated to specifically inhibit PP2A activity with the goal of enhancing effectiveness of cancer treatments that damage DNA or disrupt components of cell replication (Lu et al., 2009b). This body of work has led to generate effective membrane permeable PP2A inhibitors, such as LB-100, that are now clinically relevant for cancer therapy.

Figure 5C:
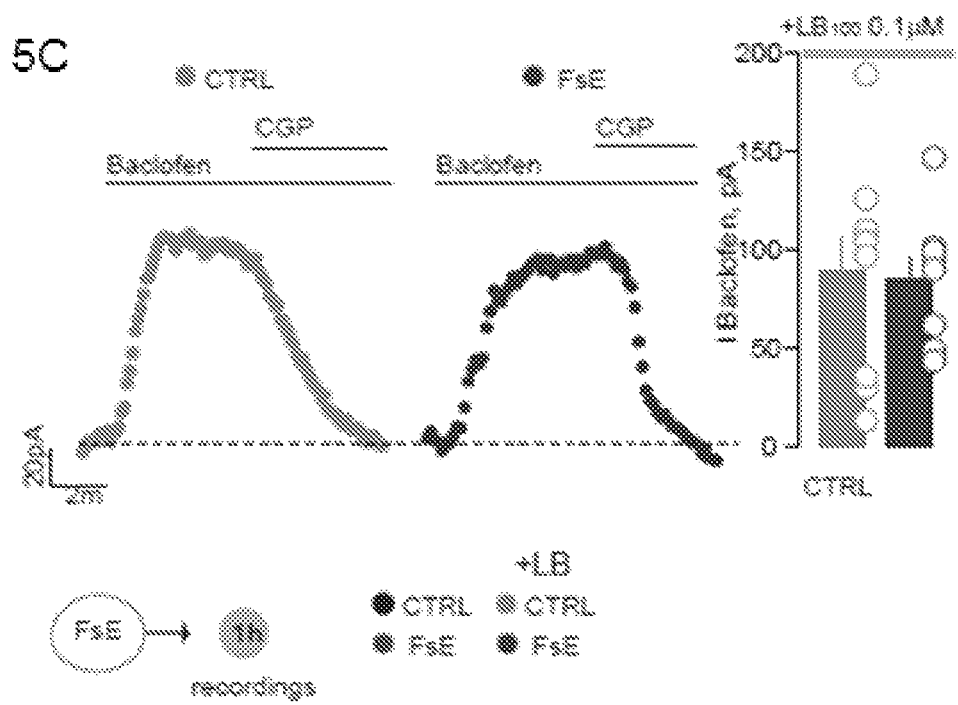
FIG. 5C: PP2A inhibition normalizes GABAB-GIRK function in the LHb after FsE. Sample traces and graph show that LB100, a selective cell permeable PP2A inhibitor applied in the bath (0.1 μM), is sufficient to rescue the FsE-induced inhibition of GABAB-GIRK currents (CTRL vs FsE; n=9 vs 9; 3 vs 3 mice; 88.41±18.64 pA vs 85.09±0.67 pA; ttest, t16=0.15, p=0.88).

Specific inhibition of PP2A activity in acute brain slices by LB-100 (0.1 µM) was tested. When in presence of LB-100 in the bath, I-Baclofen in control and FsE mouse slices were comparable (FIG. 5C). These data strengthen the hypothesis that persistent PP2A activity after FsE mediates GABAB-GIRK signaling reduction. These results show that FsE leads to GABABRs and GIRK channels internalization and functional reduction.

Figure 5D:
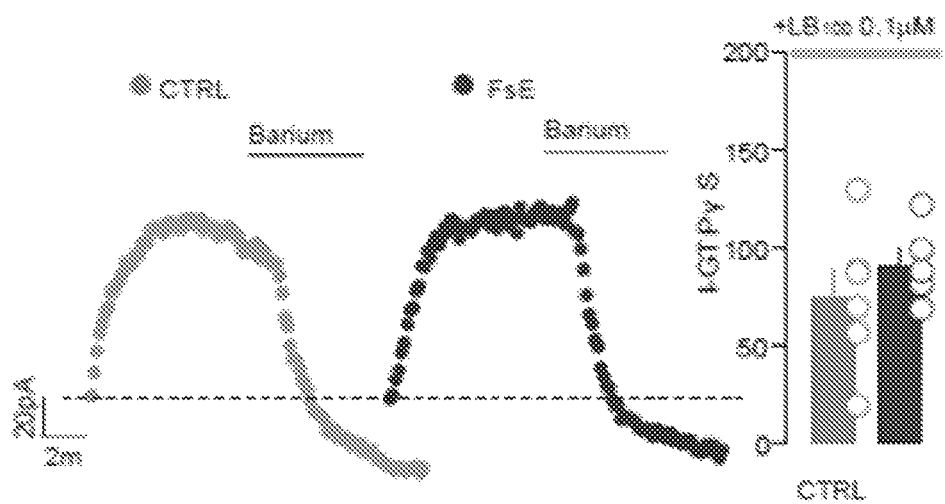
FIG. 5D: PP2A inhibition normalizes GABAB-GIRK function in the LHb after FsE. When applied in the bath, LB100 restored the $Ba^{2+}$ sensitive I-GTPγS in FsE animals. Traces and bar graph with singles plot reporting no difference between groups (CTRL vs FsE; n=6 vs 6; 3 vs 3 mice; 94.27±13.29 pA vs 110.6±20.79 pA; t-test, t10=0.66, p=0.52).

To address whether inhibition of PP2A activity rescues solely GABAB-Rs expression and function, or also GIRKs expression and function, intrapatch dialysis of GTPγS were employed to again activate GIRKs independently of GABABRs. It was found that, in presence of LB-100, I-Baclofen in LHb neurons from FsE mice were comparable to the control group (FIG. 5D). Altogether, this indicates that, not only GABAB-Rs, but also GIRK signaling or functional G protein coupling is restored when inhibiting PP2A activity (FIG. 5C, D).

Taken together, these findings suggest that foot shock experience triggers a phosphatase-dependent downregulation of GABAB-GIRK complex from the plasma membrane of LHb neurons, thereby reducing GABABR-GIRK signaling.

Example 6. Loss of GADAbR-dependent Inhibition of LHb Neuron Firing

GABAB-mediated activation of Kir3 channels produces slow inhibitory postsynaptic potentials by inducing K+ efflux thereby hyperpolarizing the cell membrane and shunting neuronal firing (Pinard et al., 2010). The data herein suggests that FsE increases the activity of LHb neurons, and provide a reduction in GABAB-GIRK signaling (FIGS. 1E & F; 2C). Additional experiments were performed to determine if the two functional modifications were causally linked.

Figures 6A, 6B:
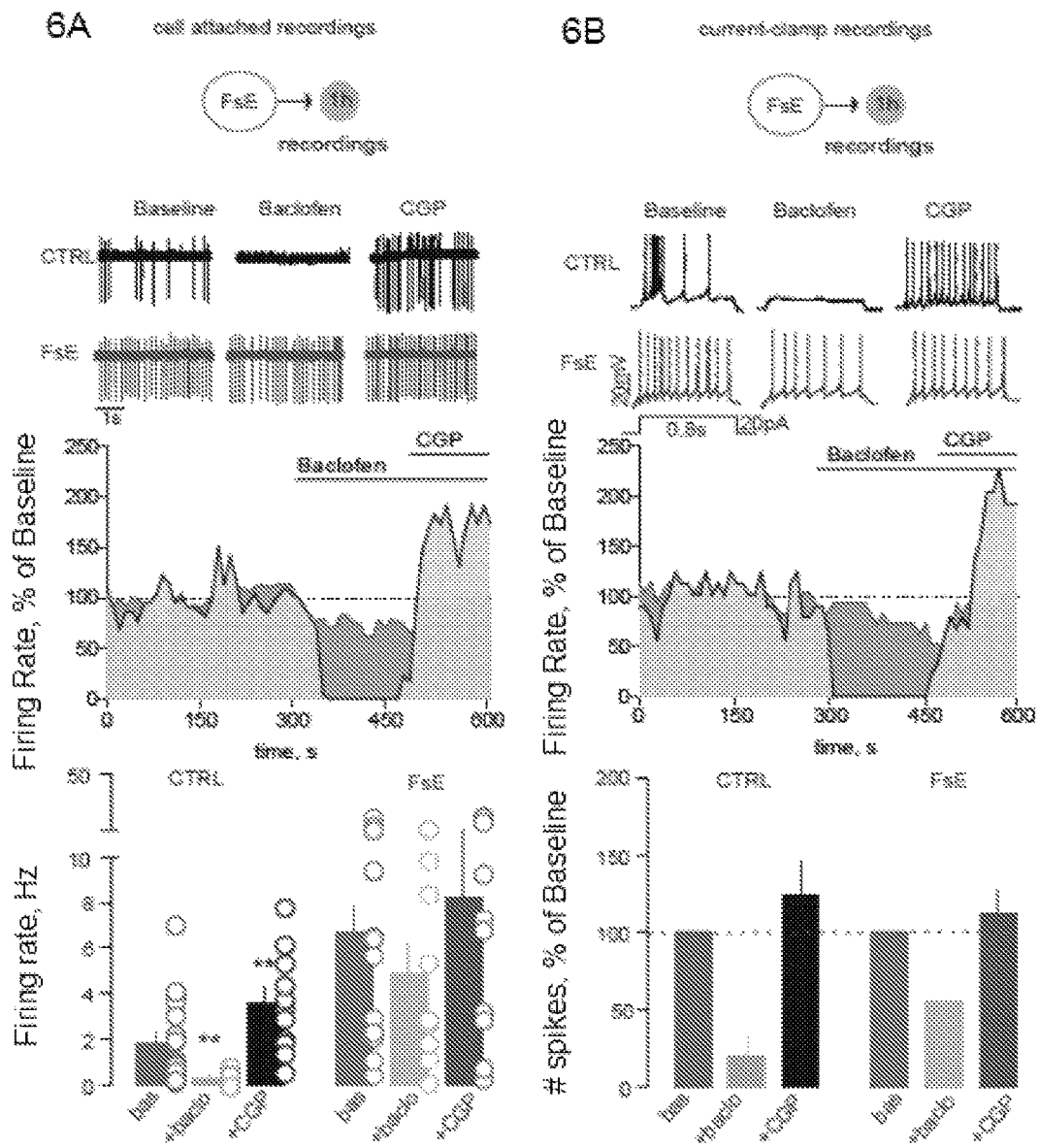
FIG. 6A: FsE-mediated hyperexcitability: loss of GABAB control on firing rate and role of PP2A activity. Example traces showing the inhibitory effect of baclofen application on the firing activity of LHb neurons recorded in a CTRL mouse (upper black trace). The GABAB antagonist CGP54626 (10 μM) revert the baclofen inhibition. Remarkably this modulatory effect of GABAB agonist and antagonist on the firing of LHb cell is reduced after the FsE (lower red trace). In the middle, the timecourse of the same examples is reported as 100% of the baseline. On the bottom, the bar graphs and scatter dot plots showing the significant change in firing rate in presence of baclofen and the further increase obtain with CGP in CTRL (Baseline vs Baclofen, CGP; n=21 vs 10, 11; 4 mice; 1.86±0.40 Hz vs 0.33±0.11 Hz, 3.62±0.65 Hz; one way ANOVA and Dunnett's test, F2,41=9.52, *p<0.05). This tuning of the firing activity is not more present in the FsE condition (Baseline vs Baclofen, CGP; n=20 vs 9, 11; 4 mice; 6.69±1.13 Hz vs 4.89±1.40 Hz, 8.23±2.25 Hz; one way ANOVA and Dunnett's test, F2,39=0.87, *p>0.05).
FIG. 6B: FsE-mediated hyperexcitability: loss of GABAB control on firing rate and role of PP2A activity. Current-clamp sample traces (20 pA injected) showing the different modulation of evoked action potentials by GABAB activation/inactivation. The graph in the middle illustrates the timecourse effect of the upper examples revealing a strong attenuation of the inhibitory influence of baclofen in FsE mice. The bar graph and scatter plot on the bottom described this effect in a larger population.

To investigate the functional consequences of depressed GABAB-GIRK currents in LHb neurons of FsE, baclofen-evoked modifications in LHb neurons output firing by recording neurons were examined in the cell-attached mode (FIG. 6A). It was predicted that a reduction in GABAB-GIRK signaling would not only increase firing of LHb neurons at baseline (FIG. 1E), but also weaken GABAB-GIRK-induced firing suppression. Bath application of baclofen in slices from control animals, produced an almost-complete reduction of LHb neuronal firing, which was promptly recovered and overshooted by CGP52536 (FIG. 6A). Conversely, in slices from FsE mice, LHb neurons presented higher basal firing in average (see also FIG. 1E), which was only mildly reduced by baclofen bath application (FIG. 6A).

Figure 6C:
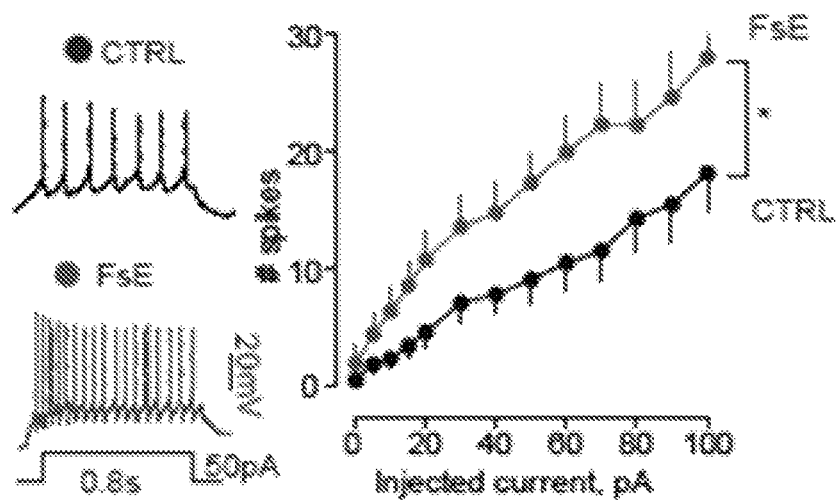
FIG. 6C: FsE-mediated hyperexcitability: loss of GABAB control on firing rate and role of PP2A activity. The hyperexcitability of LHb induced by FsE was completely abolished when LB100 (0.1 µM) was applied in the bath. Sample traces (50 pA injected) and graph on the left show the increase in excitability in FsE mice when the recordings were performed simply in ACSF and AMPA, NMDA, GABAA blockers (CTRL vs FsE; n=14 vs 17; 4 vs 5 mice; two way ANOVA RM F1,348=7.41, *p=0.02). Adding PP2A activity inhibitor (sample traces and graph on the right) was sufficient to abolish FsE induced enhancement of excitability (CTRL vs FsE; n=20 vs 16; 5 vs 4 mice; two way ANOVA RM F1,408=7.41, p=0.81).
Figure 6C:
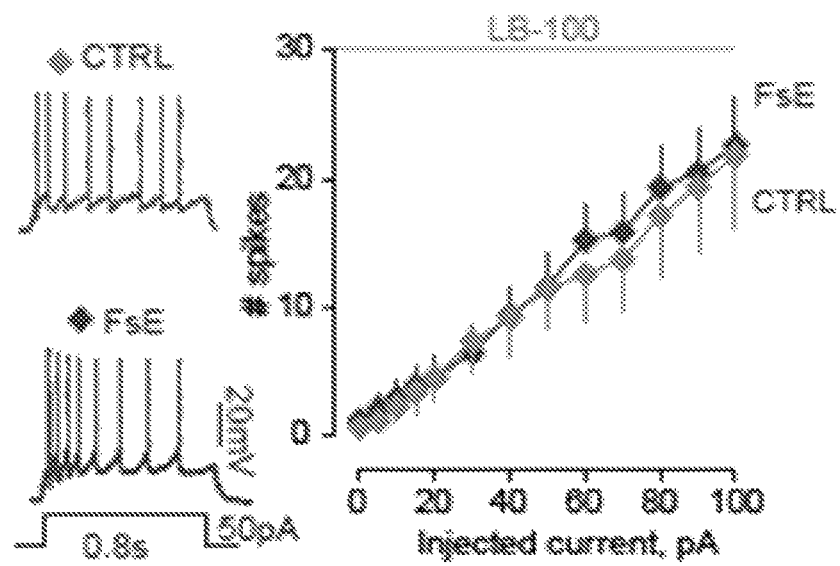

To further stress these finding, a set of experiments were performed in which whole-cell mode and current steps (20 pA) were injected to elicit a train of action potentials in LHb neurons over time. As expected, baclofen bath applications significantly depressed firing of LHb neurons recorded from control mice (FIG. 6B). By contrast, the same saturating dose of baclofen only partially decreased firing of LHb neurons in FsE animals (FIG. 6B). In order to establish whether rescuing GABAB-GIRK signaling causally recovers FsE-evoked hyperexcitability, we examined the effect of PP2A inhibition on cell excitability in control and FsE mice. As previously shown (FIG. 1F), FsE increased the input-output (I-O) relationship, and LHb neurons after FsE present a top/left-shifted I-O curve (FIG. 6C). In contrast, when LB-100 was applied, allowing inhibition of PP2A activity, I-O curves in slices from FsE mice were comparable to control conditions (FIG. 6C).

Altogether these results demonstrate that a loss of GABABR-GIRK currents in LHb neurons renders neurons more excitable and less sensitive to baclofen-driven inhibition. Moreover, PP2A inhibition may represent a viable pharmacological tool to rescue FsE-evoked cellular modifications in the LHb.

Figure 7A:
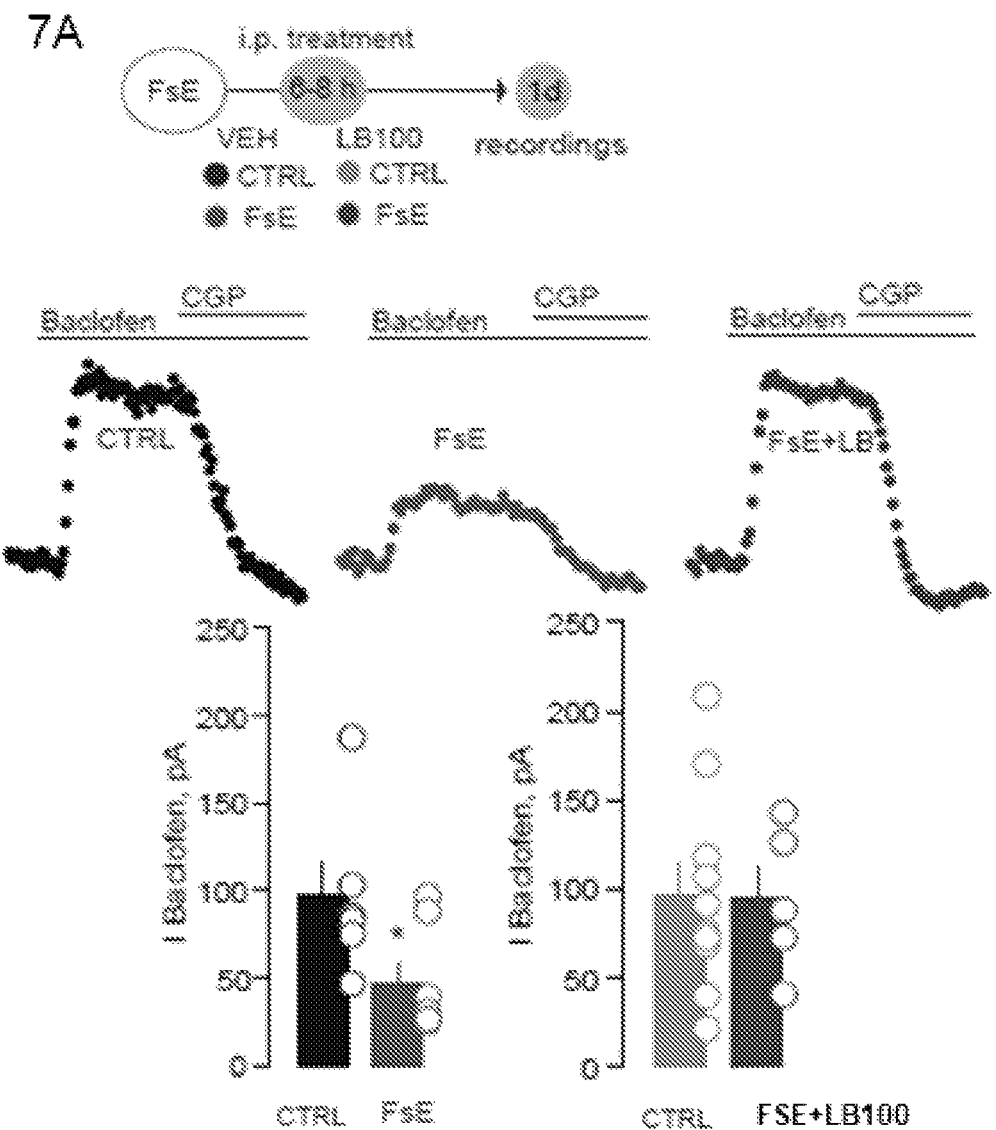
FIG. 7A: In vivo inhibition of PP2A activity rescues GABAB-GIRK function, the hyperexcitability and FsE-driven depressive-like phenotype. Schematic illustrating the in vivo experimental protocol and the timeline of experiments.
Figure 7B:
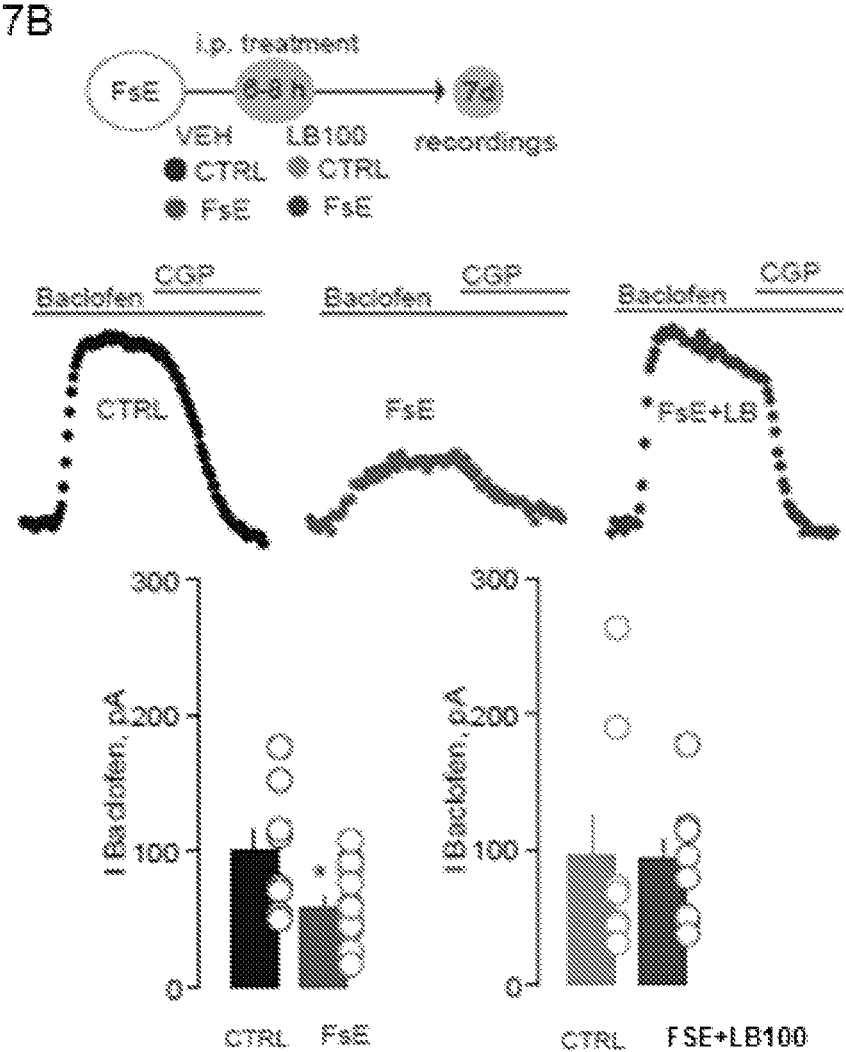
FIG. 7B: In vivo inhibition of PP2A activity rescues GABAB-GIRK function, the hyperexcitability and FsE-driven depressive-like phenotype. Sample traces, graph and scatter plot of the I-baclofen recorded one day after the FsE in animals treated with saline (sal) or LB100 (LB, 1.5 mg/kg ip). The I-baclofen attenuation recorded in FsE mice treated with sal (CTRL vs FsE; n=6 vs 7, 3 vs 3 mice; 96.75±19.64 pA vs 47.39±11.82 pA; t-test, t11=2.23, *p=0.04) is not present in the FsE group injected with LB (CTRL vs FsE; n=5 vs 10, 2 vs 3 mice; 93.88±18.37 pA vs 97.00±18.05 pA; t-test, t13-0.11, p=0.91).
Figure 7C:
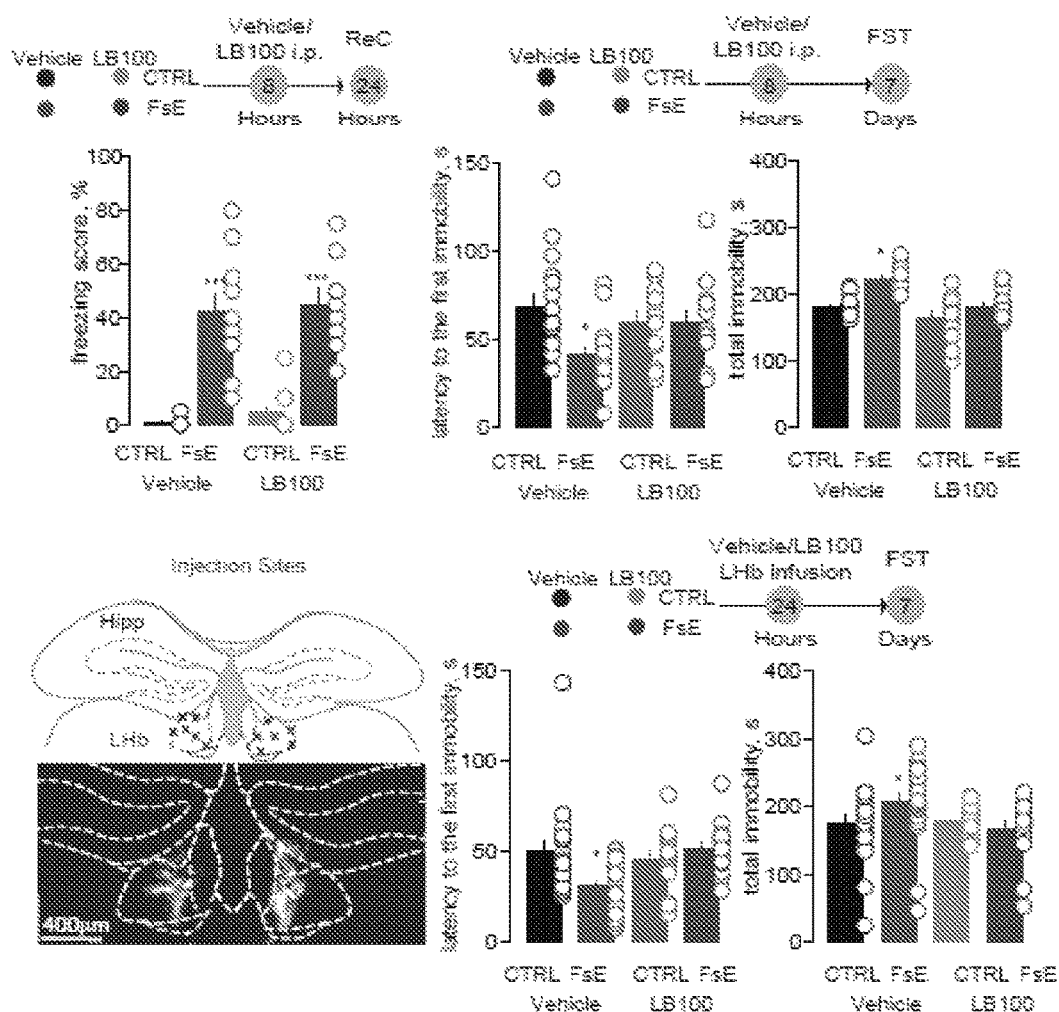
FIG. 7C: In vivo inhibition of PP2A activity rescues GABAB-GIRK function, the hyperexcitability and FsE-driven depressive-like phenotype. The reduction of GABAB-GIRK functionality was still present 7 days after the shock exposure in animal treated with sal (CTRL vs FsE; n=8 vs 14, 3 vs 4 mice; 99.85±16.38 pA vs 58.31±7.62 pA; t-test, t20=2.62, *p=0.016). A single injection of LB100 6-8 hours after the shock was able to revert the FsE-induced a decrease in I-baclofen 7 days later. (CTRL vs FsE; n=8 vs 9, 3 vs 3 mice; 95.54±30.00 pA vs 92.97±14.84 pA; t-test, t15=0.079, p=0.93).
Figure 7D:
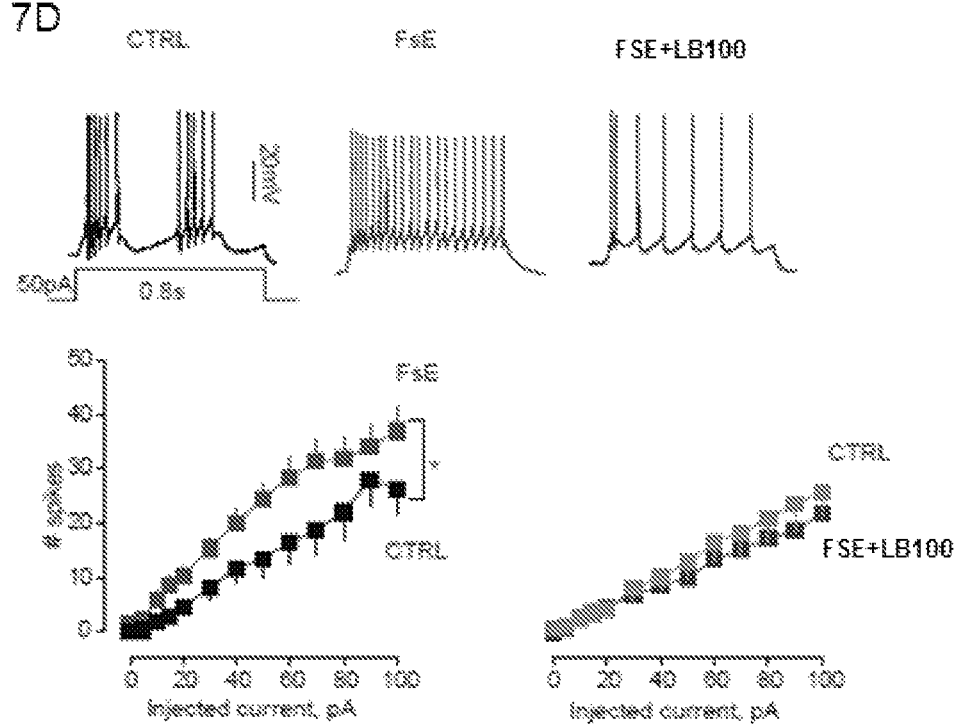
FIG. 7D: In vivo inhibition of PP2A activity rescues GABAB-GIRK function, the hyperexcitability and FsE-driven depressive-like phenotype. Sample traces (50 pA injected) and input-output curve obtained one day after the protocol and the treatment, reporting the higher excitability in FsE mice treated with sal compared to their controls (CTRL vs FsE; n=14 vs 13; 3 vs 4 mice; two way ANOVA RM F1,300=4.71, *p=0.04). Animals treated with LB100 did not show any difference in the input-output curve (CTRL vs FsE; n=15 vs 12; 4 vs 3 mice; two way ANOVA RM F1,300=0.43, p=0.52).

Example 7. PP2A Inhibition In Vivo Restores GAB-GIRK Function and Ameliorates FsEdriven Depressive Phenotypes It has been shown herein that FsE decreases GABAB-GIRK signaling and promotes hyperexcitability of LHb neurons, through a PP2A-dependent internalization of the GABAB-GIRK complex. As a consequence, it was predicted that inhibition of PP2A activity in vivo: i. would normalize FsE-induced GABAB-GIRK reduction and hyperexcitability and ii. would rescue FsE-driven depressive-like phenotype as a consequence of the recovered LHb activity. To test the first prediction, FsE mice were systemically treated them with vehicle or LB-100 (1.5 mg/Kg) 6-8 hours after the paradigm, a time point at which I-Baclofen is reduced (FIG. 2A-C). At this concentration LB-100 efficiently inhibits PP2A activity for about 12 hours, with a peak of its activity at ~8 hours (Lu et al., 2009b). LHb-containing slices were prepared one or seven days after FsE. It was observed that FsE vehicle-treated mice had significantly smaller I-Baclofen compared to control vehicle-treated animals. In contrast, I-Baclofen was comparable between the control and FsE group after systemic injections of LB-100 at one day as well as seven days after FsE (FIG. 7C, D). This indicates that, in vivo inhibition of PP2A activity rescues the FsE-evoked plasticity of GABAB-GIRK signaling.

Figure 7E:
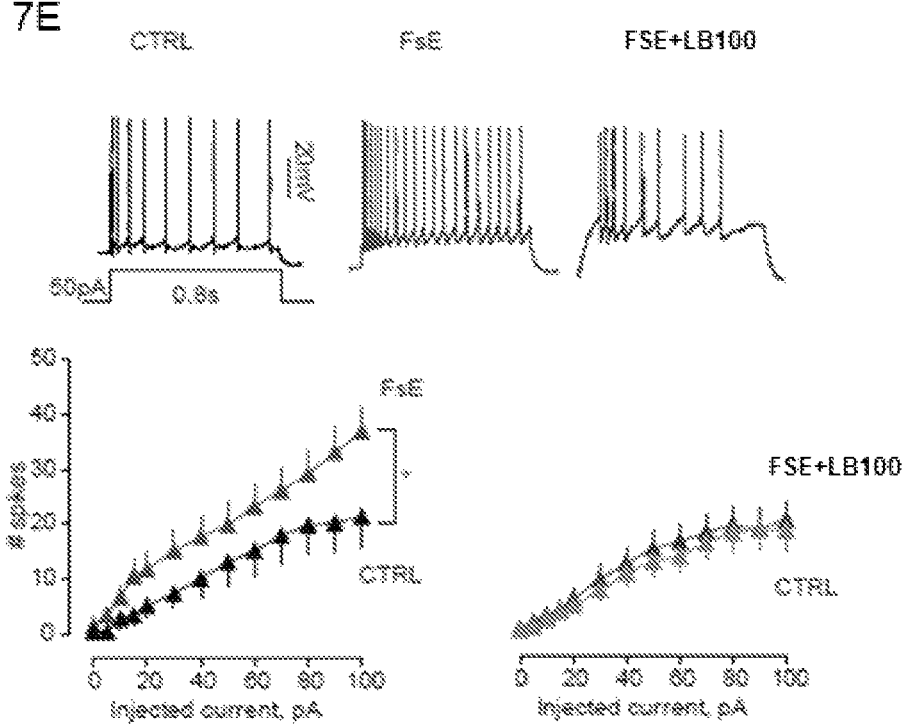
FIG. 7E: In vivo inhibition of PP2A activity rescues GABAB-GIRK function, the hyperexcitability and FsE-driven depressive-like phenotype. Same as FIG. 7D but the in vitro recordings were performed 7 days after. The excitability in animal treated with sal still differs between CTRL and FsE (CTRL vs FsE; n=15 vs 24; 3 vs 5 mice; two way ANOVA RM F1,444=5.19, *p=0.02). As at day 1 also at day 7 a single injection of LB100 6-8 hours after the FsE was able to abolish the increase in excitability (CTRL vs FsE; n=16 vs 19; 3 vs 4 mice; two way ANOVA RM F1,396=0.20, p=0.65).

It was next explored whether the rescue of GABAB-GIRK currents by PP2A inhibition was also accompanied by a functional rescue of LHb neuronal activity. LHb neuronal excitability were recorded in whole-cell mode. FsE animals vehicle-treated, as previously shown (FIG. 1F; 6C), exhibited a top/left-shift in the I-O curve at one day and seven days post FsE (FIG. 7E). Conversely, in FsE mice, LB-100 systemic injection normalized LHb neuronal excitability (FIG. 7F), highlighting a crucial role of persistent PP2A activity in controlling GABAB-GIRKs membrane levels, that is turn fundamental for neuronal activity.

If PP2A-dependent FsE-evoked GABAB-GIRK plasticity and hyperexcitability is a necessary for behavioral responses after aversive experience, PP2A inhibition may represents a viable intervention to rescue FsE-driven depressive-like phenotype. To this end, mice were subjected (or not) to FsE and it was found that one day after re-exposure to the context produced high levels of freezing only in FsE mice (FIG. 7F). This behavior was not altered by systemic PP2A inhibition (FIG. 7F). Seven days after FsE, mice were tested in the FST paradigm to assess their depressive-like phenotype. In FsE vehicle-treated mice, we found reduced latency to the first immobility along with an increased total immobility. In contrast the treatment with LB-100 led to a behavioral normalization of FsE-driven depressive-like phenotype, as latency to the first immobility and total immobility were comparable between control and FsE group (FIG. 7G). These findings establish a link between the GABAB-GIRK function, their role in controlling LHb neuronactivity and the behavioral response to the exposure to an aversive condition.

Example 8. Administration of LB-100

An amount of compound LB-100 is administered to a subject afflicted with a depressive disorder, stress disorder or addiction. The amount of the compound is effective to treat the subject.

An amount of compound LB-100 is administered to a subject following a traumatic event experienced by the subject. The amount of the compound is effective to prevent a depressive or stress disorder from afflicting the subject following the traumatic event or reduce the severity of a depressive or stress disorder that afflicts the subject following the traumatic event.

An amount of compound LB-100 is administered to a subject afflicted with a depression or PTSD. The amount of the compound is effective to treat the subject.

Example 9. Administration of LB-100 Analogs

An amount of any one of the compounds of the present invention, which are analogs of LB-100, is administered to a subject afflicted with a depressive disorder, stress disorder or addiction. The amount of the compound is effective to treat the subject.

An amount of any one of the compounds of the present invention, which are analogs of LB-100, is administered to a subject following a traumatic event experienced by the subject. The amount of the compound is effective to prevent a depressive or stress disorder from afflicting the subject following the traumatic event or reduce the severity of a depressive or stress disorder that afflicts the subject following the traumatic event.

An amount of any one of the compounds of the present invention, which are analogs of LB-100, is administered to a subject afflicted with a depression or PTSD. The amount of the compound is effective to treat the subject.

Example 10. Administration to Substance Addicted Subjects

An amount of compound LB-100 is administered to a subject suffering from a depressive or stress disorder caused by an addictive substance or caused by discontinuing use of an addictive substance. The amount of the compound is effective to treat the subject.

An amount of compound LB-100 is administered to a subject suffering from a depressive or stress disorder induced by withdrawal from the use of an addictive substance. The amount of the compound is effective to treat the subject.

An amount of any one of the compounds of the present invention, which are analogs of LB-100, is administered to a subject suffering from a depressive or stress disorder caused by an addictive substance or caused by discontinuing use of an addictive substance. The amount of the compound is effective to treat the subject.

An amount of any one of the compounds of the present invention, which are analogs of LB-100, is administered to a subject suffering from a depressive or stress disorder induced by withdrawal from the use of an addictive substance. The amount of the compound is effective to treat the subject.

An amount of compound LB-100 is administered to a subject suffering from a depressive or stress disorder and addicted to an addictive substance. The amount of the compound is effective to treat the subject.

An amount of any one of the compounds of the present invention, which are analogs of LB-100, is administered to a subject suffering from a depressive or stress disorder and addicted to an addictive substance. The amount of the compound is effective to treat the subject.

Discussion

Cellular Mechanisms Underlying GABAB-GIRK Plasticity in the LHb

Pharmacological approaches revealed that most (~80%) of the direct inhibitory effect of GABABR activation in LHb neurons can be attributed to GIRK channel activation. Importantly, exposure to aversive events selectively depressed the dominant GIRKdependent component of I-Baclofen, without modifying the GABAB-dependent GIRK-independent pathway. The FsE-induced weakening of GABAB-GIRK currents in LHb neurons could rely on alternative processes including modifications in G protein coupling (Labouebe et al., 2007) or internalization of the receptors or channels (Guetg et al., 2010; Hearing et al., 2013; Padgett et al., 2012; Terunuma et al., 2010). In support of the latter scenario, quantitative immunogold electron microscopy revealed a significant reduction in the membrane expression of GABAB receptors and GIRK channels in LHb neurons previously exposed to a foot-shock paradigm. The endocytosis rate of GABAB-$R_5$ in cortical, hippocampal, and GABA neurons of the midbrain, requires the balance of AMP-activated protein kinase (AMPK)-dependent phosphorylation of GABAB2-S783 and PP2A-dependent dephosphorylation of GABAB receptors (Gonzalez-Maeso et al., 2003; Padgett et al., 2012; Terunuma et al., 2010). The FsE evoked persistent depression of the GABAB-GIRK signaling and the rapid recovery obtained with phosphatase inhibitors suggests that PP2A activity controls the balance between membrane and intracellular GABAB receptors (Padgett et al., 2012).

Although the data suggests that CaMKII is not involved in maintaining GABAB-GIRK internalization, one cannot rule out potential implications of CaMKII or PKA at different time points as they also target specific residues of GABAB-$R_s$ subunits and control their membrane expression and surface stability (Gonzalez-Maeso et al., 2003; Guetg et al., 2010; Terunuma et al., 2010). While these mechanisms control traffic of GABAB receptors, it was found that endocytosis of GIRK channels also occurs after aversive experience. Recent evidence suggests that GIRK channels internalize via association with GABAB receptors in a macromolecular signaling complex (Hearing et al., 2013; Padgett et al., 2012). Indeed, both in the ventral tegmental area and medial prefrontal cortex drug experience promotes the internalization of GABAB-Rs and GIRK channels (Lalive et al., 2014; Lavine et al., 2002; Nobles et al., 2005; Riven et al., 2006) and can traffic together through intracellular compartments (Clancy et al., 2007).

G-protein-insensitive inwardly rectifying K+ channels (kir2) bear similar PDZ domains and have been shown to be regulated by proteins of the postsynaptic density like SAP-97 and PSD-93, leading to increased stability at the membrane (Leonoudakis et al., 2004; Leyland and Dart, 2004). It has been shown that the LHb contains protein of the four GIRKs subunits GIRK1-4. As shown previously, GIRK2c and GIRK3 contain a C-terminal tail containing a PDZ binding domain implicated in GIRK channel trafficking (Lunn et al., 2007). Despite high PDZ structure similarity, GIRK2c and GIRK3 do not interact with SAP-97 or PSD-95 (Hibino et al., 2000; Nehring et al., 2000). However, an interaction has been revealed with sorting nexin protein 27 (SNX27; (Lunn et al., 2007)), which specifically recognizes GIRK2c and GIRK3, but not Kir2.1 subunits (Balana et al., 2011). SNX27 has been reported to mediate both endosome-directed trafficking of GIRK channels and membrane trafficking of receptors like β2-adrenoreceptor (Lauffer et al., 2010), and therefore represents a potential candidate in mediating GIRK channel plasticity. Whether alternative processes such as phosphorylation of GIRK subunits changing their intrinsic properties affecting their efficacy independently of the receptor-effector coupling remains to be established (Mao et al., 2004).

GABAB-GIRK Signaling Reduction and Functional Remodeling of Neural Circuit

How does depression of GABAB-GIRK signaling in the LHb contribute to the LHb contact DA neurons in the ventral tegmental area, and, to a large extent, midbrain GABA neurons (including RMTg and VTA)? It was also found that FsE-evoked GABAB-GIRK plasticity occurs throughout the LHb, with no apparent territorial specificity. This indicates that diverse neuronal populations in the LHb undergo similar changes that impact on parallel downstream midbrain targets, and be instrumental for depressive-like phenotype (Meye Valentinova Lecca et al., 2015).

Behavioral Consequences after Aversive Experience?

GABAB-GIRK complexes control the excitability of many neuronal populations throughout the central nervous system in both physiological and pathological conditions (Luscher and Slesinger, 2010). We show that, in the LHb, pharmacological GABAB activation readily suppresses LHb firing (FIG. 5A, B). This inhibitory control is lacking after aversive experience, thereby increasing the firing rate of LHb neurons. This may have profound impact on downstream targets as the endogenous activity of LHb glutamatergic outputs conveys information related to aversion. Similarly to this study, exposure to a single session of unpredicted foot-shock increase excitatory drive, likely via a presynaptic mechanism onto midbrain GABA neurons (Stamatakis and Stuber, 2012). Further, activation of LHb terminals onto midbrain midbrain neurons also drive conditioned place aversion (Lammel et al., 2012). This is in line with anatomical evidence that axons from the Indeed, Altered midbrain inhibitory control has been implicated in several psychiatric disorders, including responses to aversive stimuli, depression, and addiction (Jhou et al., 2009; Luscher and Slesinger, 2010; Tye et al., 2013). Therefore, targeting inhibitory signaling may represent an innovative strategy for therapeutic interventions in modern neuropsychiatry.

Molecular Mechanisms in LHb for FsE-induced Depressive-like Behaviors

The persistence of cellular and synaptic adaptations occurring early after experience in specific brain structures remodels neural circuit providing a substrate for behavioral adaptations (Belin and Everitt, 2008; Mameli et al., 2009). The exposure to stressors can produce lasting behavioral changes that resemble symptoms of depression in both rodents and humans (Anisman and Zacharko, 1990; Rittenhouse et al., 2002).

Accordingly, posttraumatic stress disorder and major depressive disorder are highly comorbid psychopathologies (Bleich et al., 1997). We provide data supporting that FsE-driven GABAB-GIRK functional reduction occurs rapidly and persist for up to two weeks. Furthermore, depressive-like symptoms promoted by a single aversive experience can be rescued by blocking the PP2A activity, which is alone sufficient to normalize GABAB-GIRK function in the LHb. This suggests a causal link between FsE-evoked cellular adaptations occurring in the LHb and the etiology of depressionlike phenotypes.

In line with these observations, dysfunction of LHb has been reported to be critical in the etiology of mood disorders. Notably, in the learned helplessness rodent model of depression major synaptic modifications have been suggested to mediate the maintenance of depressive-like states. Specifically, increased excitatory drive onto LHb neurons, and an overexpression of the βCaMKII are both sufficient to promote neuronal hyperexcitability and depressive-like phenotype (Li et al., 2011; Li et al., 2013; Proulx et al., 2014). A hypothetical scenario is that the early GABAB-GIRK reduction in the LHb due to a negative experience may represent a gating mechanism for consequent adaptations such βCaMKII-mediated synaptic modifications. Whether GABAB-GIRK plasticity represent a cellular substrate determinant for neuropsychiatric disorders other than depression characterized by heightened LHb neuronal excitability including drug abuse (Meye, Valentinova Lecca et al., 2015) remains to be tested.

The present findings indicate that aversion (or stress)-induced depression of GABABR signaling in LHb neurons removes a cellular "brake" on LHb neuron activity that may provide a maladaptive excitation of especially GABA neurons of the midbrain, thereby mediating an inhibition of DA neurons (Stamatakis and Stuber, 2012). Although more experiments are necessary to understand the timeline of cellular events in the LHb during highly stressful states, the rescue of GABA-GIRK signaling by targeting for instance the PP2A might open potential strategies for treating posttraumatic stress disorders or depressive-like symptoms.

Here, it was identified that GABA-GIRK signaling is a critical molecular link between FsE and its long-lasting behavioral adaptations. FsE produces delayed depressive-like behaviors and LHb neuronal hyperexcitability. We described that already after ~1 hr following FsE or similar aversive experiences, GABAB-GIRK-mediated responses in LHb neurons are persistently reduced. FsE-induced diminished GABAB-GIRK function requires GABAB and GIRK trafficking to the endoplasm, and persistent activation of the phosphatase PP2A. As a consequence, LHb neuron firing increased, and its modulation by baclofen was strongly reduced. Reducing PP2A function in vitro as well as in vivo rescues GABAB-GIRK signaling, and hyperexcitability. Finally, the pharmacological inhibition of PP2A rescues the FsE-driven depressive-like phenotypes. These findings unravel early molecular mechanism in the LHb after negative experience and highlights potential pharmacological targets to rescue behavioral adaptations driven by aversive events.

SUMMARY

Aversive conditions increase the excitability of LHb neurons, a fundamental process for the development of depressive-like phenotypes in diverse neuropsychiatric disorders (Li et al., 2013) (Meye, Valentinova, Lecca 2015). Exposure to a single session of unpredicted aversive stimuli is sufficient to significantly weaken GABAB-GIRK signaling and to increase LHb neuronal activity. Taken at face value, these modifications alone are not sufficient to cause depression but rather may represent an initial permissive step for widespread adaptations in the LHb and downstream circuits contributing to the etiology of mood disorders. The study of the early effects after a single exposure to aversive stimuli allowed us to dissect the precise molecular events underlying the aversion-evoked plasticity of GABAB-GIRK signaling in the LHb. It was demonstrated that FsE-induced reduction of I-Baclofen arises from an internalization of GABAB-Rs and GIRK channels that functionally determines hyperexcitability of LHb neurons.

Mechanistically these adaptations require a constitutive increase in PP2A activity, suggesting for a dephosphorylation-based internalization of both GABAB and GIRKs. PP2A inhibition, such as by a PP2A inhibitor of the present application, restores GABAB-GIRK signaling, LHb neuronal excitability and rescues FsE-driven depressive-like phenotype, indicating novel pharmacological targets to possibly contrast negative behavioral states after a traumatic event.

Compound LB100 (see U.S. Pat. No. 7,998,957 B2) has anti-cancer activity when used alone (Lu et al. 2009a) and significantly potentiates in vivo, without observable increase in toxicity, the anti-tumor activity of standard cytotoxic anti-cancer drugs including temozolomide (Lu et al. 2009b, Martiniova et al. 2010), doxorubicin (Zhang et al. 2010), and docetaxel. LB100 was recently approved for Phase I clinical evaluation alone and in combination with docetaxel and is in clinical trial. However, the methods described herein employ LB100 for use in treating or preventing depressive or stress disorders.

REFERENCES

Alcami, P. et al. (2012). Measuring the firing rate of high-resistance neurons with cell-attached recording. J Neurosci 32, 3118-3130.

Anisman, H., and Zacharko, R. M. (1990). Multiple neurochemical and behavioral consequences of stressors: implications for depression. Pharmacol Ther 46, 119-136.

Bagdy, G., Juhasz, G., and Gonda, X. (2012). A new clinical evidence-based gene environment interaction model of depression. Neuropsychopharmacol Hung 14, 213-220.

Balana, B. et al. (2011). Mechanism underlying selective regulation of G protein-gated inwardly rectifying potassium channels by the psychostimulant-sensitive sorting nexin 27. Proc Natl Acad Sci USA 108, 5831-5836.

Belin, D., and Everitt, B. J. (2008). Cocaine seeking habits depend upon dopamine dependent serial connectivity linking the ventral with the dorsal striatum. Neuron 57, 432-441.

Bleich, A. et al. (1997). Post-traumatic stress disorder and depression. An analysis of comorbidity. Br J Psychiatry 170, 479-482.

Boyer, S. B. et al. (2009). Direct interaction of GABAB receptors with M2 muscarinic receptors enhances muscarinic signaling. J Neurosci 29, 15796-15809.

Buynitsky, T., and Mostofsky, D. I. (2009). Restraint stress in biobehavioral research: Recent developments. Neurosci Biobehav Rev 33, 1089-1098.

Clancy, S. M., Boyer, S. B., and Slesinger, P. A. (2007). Coregulation of natively expressed pertussis toxin-sensitive muscarinic receptors with G-protein-activated potassium channels. J Neurosci 27, 6388-6399.

Cornelisse, L. N. et al. (2007). Reduced 5-HT1A- and GABAB receptor function in dorsal raphe neurons upon chronic fluoxetine treatment of socially stressed rats. J Neurophysiol 98, 196-204.

Gonzalez-Maeso, J., Wise, A., Green, A., and Koenig, J. A. (2003). Agonist-induced desensitization and endocytosis of heterodimeric GABAB receptors in CHO-K1 cells. Eur J Pharmacol 481, 15-23.

Guetg, N. et al. (2010). NMDA receptor-dependent GABAB receptor internalization via CaMKII phosphorylation of serine 867 in GABAB1. Proc Natl Acad Sci USA 107, 13924-13929.

Hammack, S. E., Cooper, M. A., and Lezak, K. R. (2012). Overlapping neurobiology of learned helplessness and conditioned defeat: implications for PTSD and mood disorders. Neuropharmacology 62, 565-575.

Hearing, M. et al. (2013). Repeated cocaine weakens GABA (B)-Girk signaling in layer 5/6 pyramidal neurons in the prelimbic cortex. Neuron 80, 159-170.

Hibino, H. et al. (2000). Anchoring proteins confer G protein sensitivity to an inward-rectifier K(+) channel through the GK domain. EMBO J 19, 78-83.

Hikosaka, O. (2010). The habenula: from stress evasion to value-based decision making. Nat Rev Neurosci 11, 503-513.

Jhou, T. C. et al. (2009). The rostromedial tegmental nucleus (RMTg), a GABAergic afferent to midbrain dopamine neurons, encodes aversive stimuli and inhibits motor responses. Neuron 61, 786-800.

Knoll, A. T., and Carlezon, W. A. J. (2010). Dynorphin, stress, and depression. Brain Res 1314, 56-73.

Labouebe, G. et al. (2007). RGS2 modulates coupling between GABAB receptors and GIRK channels in dopamine neurons of the ventral tegmental area. Nat Neurosci 10, 1559-1568.

Lalive, A. L. et al. (2014). Firing modes of dopamine neurons drive bidirectional GIRK channel plasticity. J Neurosci 34, 5107-5114.

Lauffer, B. E. et al. (2010). SNX27 mediates PDZ-directed sorting from endosomes to the plasma membrane. J Cell Biol 190, 565-574.

Lavine, N. et al. (2002). G protein-coupled receptors form stable complexes with inwardly rectifying potassium channels and adenylyl cyclase. J Biol Chem 277, 46010-46019.

Lecca, S., Meye, F. J., and Mameli, M. (2014). The lateral habenula in addiction and depressions an anatomical, synaptic and behavioral overview. Eur J Neurosci 39, 1170-1178.

Lemos, J. C. et al. (2012a). Repeated stress dysregulates kappa-opioid receptor signaling in the dorsal raphe through a p38alpha MAPK-dependent mechanism. J Neurosci 32, 12325-12336.

Lemos, J. C. et al. (2012b). Severe stress switches CRF action in the nucleus accumbens from appetitive to aversive. Nature 490, 402-406.

Leonoudakis, D. et al. (2004). A multiprotein trafficking complex composed of SAP97, CASK, Veli, and Mint1 is associated with inward rectifier Kir2 potassium channels. J Biol Chem 279, 19051-19063.

Leyland, M. L., and Dart, C. (2004). An alternatively spliced isoform of PSD-93/chapsyn 110 binds to the inwardly rectifying potassium channel, Kir2.1. J Biol Chem 279, 43427-43436.

Li, B. et al. (2011). Synaptic potentiation onto habenula neurons in the learned helplessness model of depression. Nature 470, 535-539.

Li, K. et al. (2013). betaCaMKII in lateral habenula mediates core symptoms of depression. Science 341, 1016-1020.

Logothetis, D. E. et al. (1987). The beta gamma subunits of GTP-binding proteins activate the muscarinic K+ channel in heart. Nature 325, 321-326.

Lu, J. et al. (2009a). The effect of a PP2A inhibitor on the nuclear receptor corepressor pathway in glioma Laboratory investigation. J Neurosurgery 113, No. 2, 225-233.

Lu, J. et al. (2009b). Inhibition of serine/threonine phosphatase PP2A enhances cancer chemotherapy by blocking DNA damage induced defense mechanisms. Proc Natl Acad Sci USA, 106, 11697-702.

Lujan, R. et al. (2014). New insights into the therapeutic potential of Girk channels. Trends Neurosci 37, 20-29.

Lunn, M. L. et al. (2007). A unique sorting nexin regulates trafficking of potassium channels via a PDZ domain interaction. Nat Neurosci 10, 1249-1259.

Luscher, C. et al. (1997). G protein-coupled inwardly rectifying K+ channels (GIRKs) mediate postsynaptic but not presynaptic transmitter actions in hippocampal neurons. Neuron 19, 687-695.

Luscher, C., and Slesinger, P. A. (2010). Emerging roles for G protein-gated inwardly rectifying potassium (GIRK) channels in health and disease. Nat Rev Neurosci 11, 301-315.

Luthi, A., and Luscher, C. (2014). Pathological circuit function underlying addiction and anxiety disorders. Nat Neurosci 17(12), 1635-1643.

Mameli, M. et al. (2009). Cocaine-evoked synaptic plasticity: persistence in the VTA triggers adaptations in the NAc. Nat Neurosci 12, 1036-1041.

Mao, J. et al. (2004). Molecular basis for the inhibition of G protein-coupled inward rectifier K(+) channels by protein kinase C. Proc Natl Acad Sci USA 101, 1087-1092.

Martiniova, L. et al. (2011). Pharmacologic modulation of serine/threonine phosphorylation highly sensitizes PHEO in a MPC cell and mouse model to conventional chemotherapy. PLoS One 6, e14678.

Matsumoto, M., and Hikosaka, O. (2007). Lateral habenula as a source of negative reward signals in dopamine neurons. Nature 447, 1111-1115.

Nehring, R. B. et al. (2000). Neuronal inwardly rectifying K(+) channels differentially couple to PDZ proteins of the PSD-95/SAP90 family. J Neurosci 20, 156-162.

Nobles, M., Benians, A., and Tinker, A. (2005). Heterotrimeric G proteins precouple with G protein-coupled receptors in living cells. Proc Natl Acad Sci USA 102, 18706-18711.

Padgett, C. L. et al. (2012). Methamphetamine-evoked depression of GABA(B) receptor signaling in GABA neurons of the VTA. Neuron 73, 978-989.

Pinard, A., Seddik, R., and Bettler, B. (2010). GABAB receptors: physiological functions and mechanisms of diversity. Adv Pharmacol 58, 231-255.

Porsolt, R. D., Bertin, A., and Jalfre, M. (1977). Behavioral despair in mice: a primary screening test for antidepressants. Arch Int Pharmacodyn Ther 229, 327-336.

Proulx, C. D., Hikosaka, O., and Malinow, R. (2014). Reward processing by the lateral habenula in normal and depressive behaviors. Nat Neurosci 17, 1146-1152.

Rittenhouse, P. A. et al. (2002). Amplified behavioral and endocrine responses to forced swim stress in the Wistar-Kyoto rat. Psychoneuroendocrinology 27, 303-318.

Riven, I., Iwanir, S., and Reuveny, E. (2006). GIRK channel activation involves a local rearrangement of a preformed G protein channel complex. Neuron 51, 561-573.

Shabel, S. J., Proulx, C. D., Piriz, J., and Malinow, R. (2014). Mood regulation. GABA/glutamate co-release controls habenula output and is modified by antidepressant treatment. Science 345, 1494-1498.

Stamatakis, A. M., and Stuber, G. D. (2012). Activation of lateral habenula inputs to the ventral midbrain promotes behavioral avoidance. Nat Neurosci 15, 1105-1107.

Takahashi, L. K., Nakashima, B. R., Hong, H., and Watanabe, K. (2005). The smell of danger: a behavioral and neural analysis of predator odor-induced fear. Neurosci Biobehav Rev 29, 1157-1167.

Terunuma, M., Pangalos, M. N., and Moss, S. J. (2010). Functional modulation of GABAB receptors by protein kinases and receptor trafficking. Adv Pharmacol 58, 113-122.

Tiao, J. Y. et al. (2008). The sushi domains of secreted GABA(B1) isoforms selectively impair GABA(B) heteroreceptor function. J Biol Chem 283, 31005-31011.

Tye, K. M. et al. (2013). Dopamine neurons modulate neural encoding and expression of depression-related behaviour. Nature 493, 537-541.

Zhang C, et al. (2010). A synthetic cantharidin analog for the enhancement of doxorubicin suppression of stem cell-derived aggressive sarcoma. Biomaterials 31, 9535-43.

Zucker, R. S., and Regehr, W. G. (2002). Short-term synaptic plasticity. Annu Rev Physiol 64, 355-405.

What is claimed is:

1. A method of treating major depression in a subject afflicted therewith comprising administering to the subject an effective amount of a compound having the structure:

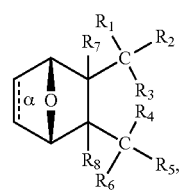

wherein bond α is present or absent;

$R_1$ and $R_2$ together are =O;

$R_3$ is OH, O⁻, OR$_9$, O (CH$_2$)$_{1-6}$R$_9$, SH, S⁻, or SR$_9$, wherein $R_9$ is H, alkyl, alkenyl, alkynyl or aryl;

$R_4$ is

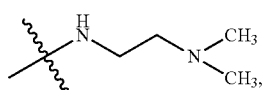

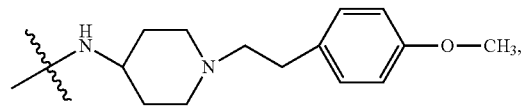

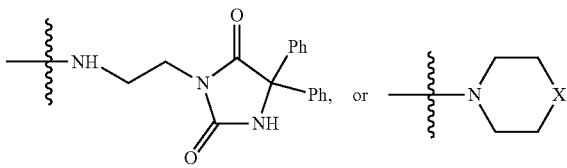

where X is O, S, NR$_{10}$, N⁺HR$_{10}$ or N$^{+R}{}_{10}$R$_{10}$, where each $R_{10}$ is independently H, alkyl, alkenyl, alkynyl, aryl,

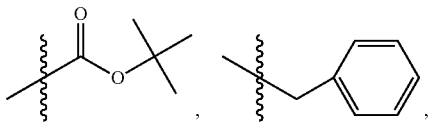

—CH$_2$CN, —CH$_2$CO$_2$R$_{11}$, or —CH$_2$COR$_{11}$, wherein each $R_{11}$ is independently H, alkyl, alkenyl or alkynyl;

$R_5$ and $R_6$ taken together are =O;

$R_7$ and $R_8$ are each H, or a salt, zwitterion, or ester thereof, so as to thereby treat the depressive or stress disorder in the subject.

2. The method of claim 1, wherein the amount of the compound is effective to reduce a clinical symptom of the major depression in the subject.

3. The method of claim 1, wherein the treating comprises reducing the activity of the lateral habenula of the subject.

4. The method of claim 1, wherein the treating comprises reducing the activity of neurons in the lateral habenula of the subject.

5. The method of claim 1, wherein the treating comprises reducing neuronal hyperexcitability in the lateral habenula of the subject, or restoring normal GABAB-GIRK function in the lateral habenula of the subject.

6. The method of claim 1, wherein the treating comprises inhibiting phosphatase activity in the lateral habenula of the subject.

7. The method of claim 1, wherein the compound has the structure

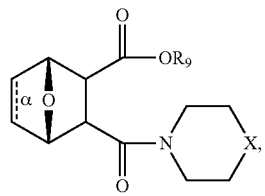

wherein bond α is present or absent;

$R_9$ is present or absent and when present is H, alkyl, alkenyl, alkynyl or phenyl; and X is O, NR$_{10}$, NH⁺R$_{10}$ or N⁺R$_{10}$R$_{10}$, where each $R^{10}$ is independently H, alkyl, substituted alkyl, alkenyl, substituted alkenyl, alkynyl, substituted alkynyl, aryl,

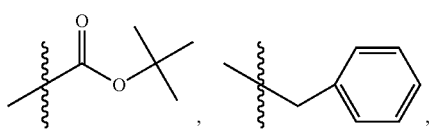

—CH$_2$CN, —CH$_2$CO$_2$R$_{12}$, or —CH$_2$COR$_{12}$, where $R_{12}$ is H or alkyl, or a salt, zwitterion or ester thereof.

8. The method of claim 1, wherein the compound has the structure

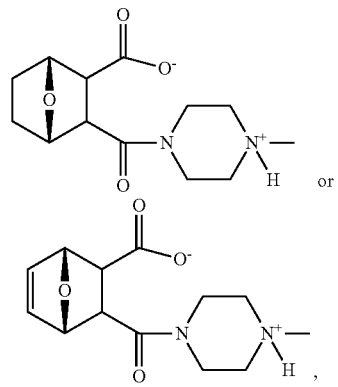

or a salt or ester thereof.

9. The method of claim 1, wherein the amount of the compound administered to the subject is 0.1 mg/m² to 5 mg/m².

10. The method of claim 9, wherein the amount of the compound is administered once daily, once weekly, or once monthly.

11. A method of treating post-traumatic stress disorder (PTSD) in a subject afflicted therewith in a subject following a traumatic event comprising administering to the subject an effective amount of a compound having the structure:

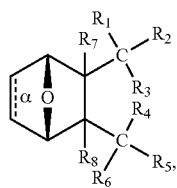

wherein
  bond α is present or absent;
  $R_1$ and $R_2$ together are =O;
  $R_3$ is OH, O⁻, $OR_9$, O $(CH_2)_{1-6}R_9$, SH, S⁻, or $SR_9$,
    wherein $R_9$ is H, alkyl, alkenyl, alkynyl or aryl;
  $R_4$ is

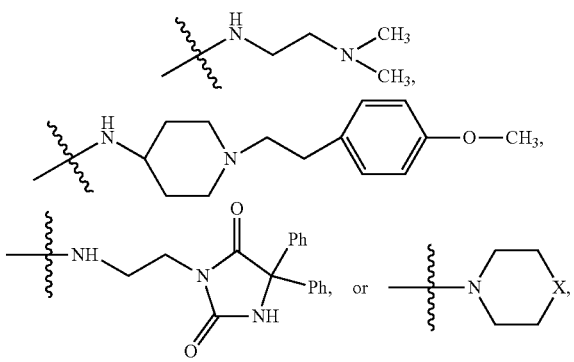

where X is O, S, $NR_{10}$, N⁺$HR_{10}$ or N³⁰ $R_{10}R_{10}$,
where each $R_{10}$ is independently H, alkyl, alkenyl, alkynyl, aryl,

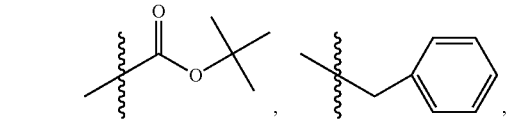

—$CH_2CN$, —$CH_2CO_2R_{11}$, or —$CH_2COR_{11}$,
  wherein each $R_{11}$ is independently H, alkyl, alkenyl or alkynyl;
  $R_5$ and $R_6$ taken together are =O;
  $R_7$ and $R_8$ are each H,
  or a salt, zwitterion, or ester thereof,
  so as to thereby treat the PTSD in the subject following a traumatic event.

12. The method of claim 11, wherein the amount of the compound is effective to reduce a clinical symptom of the PTSD in the subject.

13. The method of claim 11, wherein the treating comprises reducing the activity of the lateral habenula of the subject.

14. The method of claim 11, wherein the treating comprises reducing the activity of neurons in the lateral habenula of the subject.

15. The method of claim 11, wherein the treating comprises reducing neuronal hyperexcitability in the lateral habenula of the subject, or restoring normal GABAB-GIRK function in the lateral habenula of the subject.

16. The method of claim 11, wherein the treating comprises inhibiting phosphatase activity in the lateral habenula of the subject.

17. The method of claim 11, wherein the compound has the structure

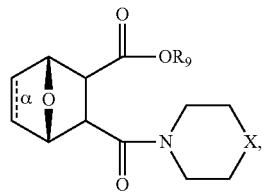

wherein
  bond α is present or absent;
  $R_9$ is present or absent and when present is H, alkyl, alkenyl, alkynyl or phenyl; and
  X is O, $NR_{10}$, $_{NH}$⁺$R_{10}$ or N⁺$R_{10}R_{10}$,
    where each $R^{10}$ is independently H, alkyl, substituted alkyl, alkenyl, substituted alkenyl, alkynyl, substituted alkynyl, aryl,

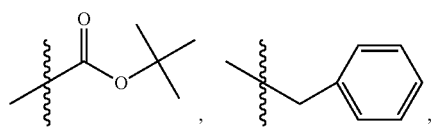

—$CH_2CN$, —$CH_2CO_2R_{12}$, or —$CH_2COR_{12}$,
  where $R_{12}$ is H or alkyl,
  or a salt, zwitterion or ester thereof.

18. The method of claim 11, wherein the compound has the structure

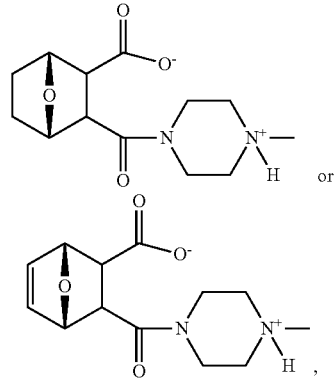

or a salt or ester thereof.

19. The method of claim 11, wherein the amount of the compound administered to the subject is 0.1 mg/m² to 5 mg/m².

20. The method of claim 19, wherein the amount of the compound is administered once daily, once weekly, or once monthly.

* * * * *